United States Patent [19]

Green et al.

[11] Patent Number: 5,725,537
[45] Date of Patent: *Mar. 10, 1998

[54] METHOD OF PERFORMING A VESSEL ANASTOMOSIS USING A SURGICAL CLIP APPLIER

[75] Inventors: David T. Green, Westport; Henry Bolanos, Norwalk; Kenneth E. Toso, Wilton; Daniel E. Alesi, Sherman; Robert J. Geiste, Milford; Frank C. Maffei, Shelton, all of Conn.

[73] Assignee: United States Surgical Corporation, Norwalk, Conn.

[*] Notice: The term of this patent shall not extend beyond the expiration date of Pat. No. 5,720,756.

[21] Appl. No.: 713,733

[22] Filed: Sep. 13, 1996

Related U.S. Application Data

[63] Continuation of Ser. No. 467,952, Jun. 6, 1995, abandoned, which is a continuation of Ser. No. 311,049, Sep. 23, 1994, abandoned, which is a continuation-in-part of Ser. No. 134,017, Oct. 8, 1993, abandoned, which is a continuation-in-part of Ser. No. 959,201, Oct. 9, 1992, abandoned.

[51] Int. Cl.$^6$ ...................................................... A61B 17/00
[52] U.S. Cl. ........................... 606/143; 606/139; 606/153; 227/901
[58] Field of Search ........................ 606/139, 142, 606/143, 151, 153, 155, 1, 205–207; 227/901, 19, 175.1–182; 29/243.56

[56] References Cited

U.S. PATENT DOCUMENTS

| | | |
|---|---|---|
| 2,968,041 | 1/1961 | Skold . |
| 3,152,336 | 10/1964 | Brady . |
| 3,232,089 | 2/1966 | Samuels et al. . |
| 3,646,801 | 3/1972 | Caroli . |
| 3,753,438 | 8/1973 | Wood et al. . |
| 3,777,538 | 12/1973 | Weatherly et al. . |
| 4,152,920 | 5/1979 | Green . |
| 4,201,314 | 5/1980 | Samuels et al. . |
| 4,202,480 | 5/1980 | Annett . |
| 4,242,902 | 1/1981 | Green . |
| 4,256,251 | 3/1981 | Moshofsky . |
| 4,296,751 | 10/1981 | Blake, III et al. . |
| 4,299,224 | 11/1981 | Noiles . |
| 4,316,468 | 2/1982 | Klieman et al. . |
| 4,317,535 | 3/1982 | Huftel et al. . |
| 4,325,376 | 4/1982 | Klieman et al. . |
| 4,372,316 | 2/1983 | Blake, III et al. . |
| 4,408,603 | 10/1983 | Blake, III et al. . |
| 4,425,915 | 1/1984 | Ivanov . |
| 4,427,008 | 1/1984 | Transue . |
| 4,430,997 | 2/1984 | DiGiovanni et al. . |
| 4,452,357 | 6/1984 | Klieman et al. . |
| 4,452,376 | 6/1984 | Klieman et al. . |
| 4,462,404 | 7/1984 | Schwarz et al. . |
| 4,471,780 | 9/1984 | Menges et al. . |

(List continued on next page.)

FOREIGN PATENT DOCUMENTS

| | | |
|---|---|---|
| 0406724 | 1/1991 | European Pat. Off. . |
| 0469524 | 2/1992 | European Pat. Off. . |
| 0507537 | 10/1992 | European Pat. Off. . |
| 8801486 | 3/1988 | WIPO . |
| 9421181 | 9/1994 | WIPO . |

*Primary Examiner*—Jeffrey A. Schmidt

[57] ABSTRACT

A surgical clip applier comprising a housing, a pair of handles pivotally connected to opposite sides of the housing, and a jaw blade assembly fixedly connected to the housing. The jaw blade assembly includes a pair of jaws for receiving and deforming a clip therebetween and a clip carrier for supplying a series of clips to the jaws. A channel assembly is slidably mounted with respect to the housing and envelops the jaw blade assembly for camming the jaws closed upon closing of the handles. The clips may be fed to the jaws by a spring biased feed bar which operates upon closing of the handles, or may be urged by pusher bar which provides a biasing force to the clips to be retained by the jaws. The instrument may be used in conventional surgical procedures, or may be adapted for endoscopic and laparoscopic surgical procedures requiring the application of microsurgical clips.

14 Claims, 21 Drawing Sheets

U.S. PATENT DOCUMENTS

| | | |
|---|---|---|
| 4,478,220 | 10/1984 | DiGiovanni et al. . |
| 4,480,640 | 11/1984 | Becht . |
| 4,480,641 | 11/1984 | Failla et al. . |
| 4,509,518 | 4/1985 | McGarry et al. . |
| 4,512,345 | 4/1985 | Green et al. . |
| 4,522,207 | 6/1985 | Klieman et al. . |
| 4,532,925 | 8/1985 | Blake, III . |
| 4,549,544 | 10/1985 | Favaron . |
| 4,562,839 | 1/1986 | Blake, III et al. . |
| 4,565,199 | 1/1986 | Becht . |
| 4,572,183 | 2/1986 | Juska . |
| 4,576,166 | 3/1986 | Montgomery et al. . |
| 4,586,503 | 5/1986 | Kirsch et al. . |
| 4,598,711 | 7/1986 | Deniega . |
| 4,611,595 | 9/1986 | Klieman et al. . |
| 4,616,650 | 10/1986 | Green et al. . |
| 4,624,254 | 11/1986 | McGarry et al. . |
| 4,630,608 | 12/1986 | Arroyo . |
| 4,637,395 | 1/1987 | Caspar et al. . |
| 4,662,373 | 5/1987 | Montgomery et al. . |
| 4,674,504 | 6/1987 | Klieman et al. . |
| 4,712,549 | 12/1987 | Peters et al. . |
| 4,733,664 | 3/1988 | Kirsch et al. . |
| 4,850,355 | 7/1989 | Brooks et al. . |
| 4,929,240 | 5/1990 | Kirsch et al. . |
| 4,983,176 | 1/1991 | Cushman et al. . |
| 5,030,226 | 7/1991 | Green et al. . |
| 5,047,038 | 9/1991 | Peters et al. . |
| 5,049,152 | 9/1991 | Simon et al. . |
| 5,084,057 | 1/1992 | Green et al. . |
| 5,104,395 | 4/1992 | Thornton et al. . |
| 5,112,343 | 5/1992 | Thorton . |
| 5,122,150 | 6/1992 | Puig . |
| 5,156,609 | 10/1992 | Nakao et al. ............... 606/142 |
| 5,171,247 | 12/1992 | Hughett et al. . |
| 5,171,249 | 12/1992 | Stefanchik et al. . |
| 5,207,692 | 5/1993 | Kraus et al. . |
| 5,211,649 | 5/1993 | Kohler et al. . |
| 5,246,450 | 9/1993 | Thornton et al. . |
| 5,282,806 | 2/1994 | Haber et al. . |
| 5,330,487 | 7/1994 | Thornton et al. . |
| 5,370,658 | 12/1994 | Scheller et al. . |
| 5,409,498 | 4/1995 | Braddock et al. . |
| 5,431,668 | 7/1995 | Burbank, III et al. . |
| 5,501,698 | 3/1996 | Roth et al. . |

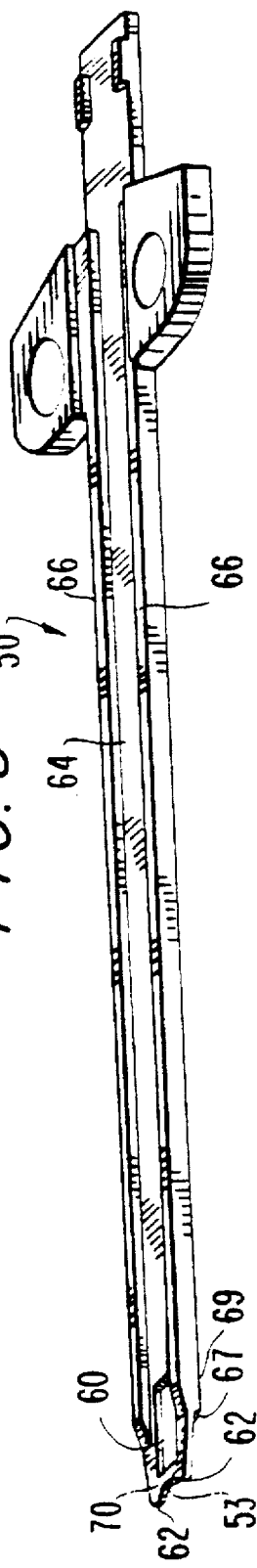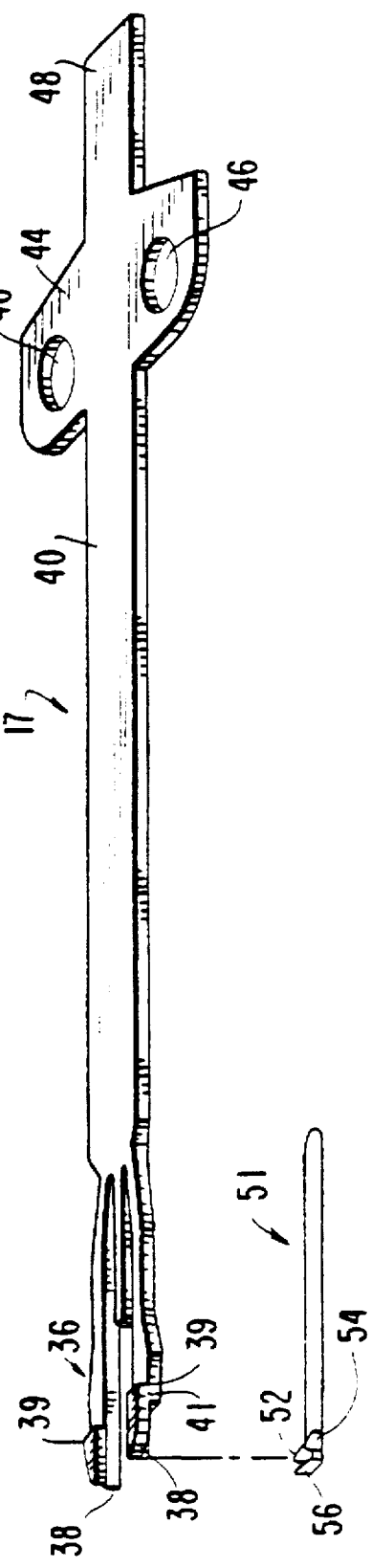

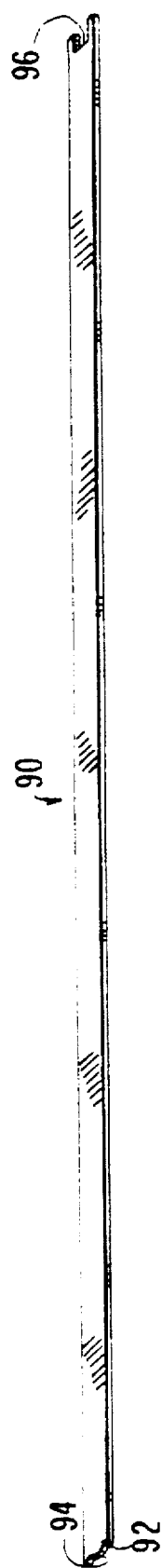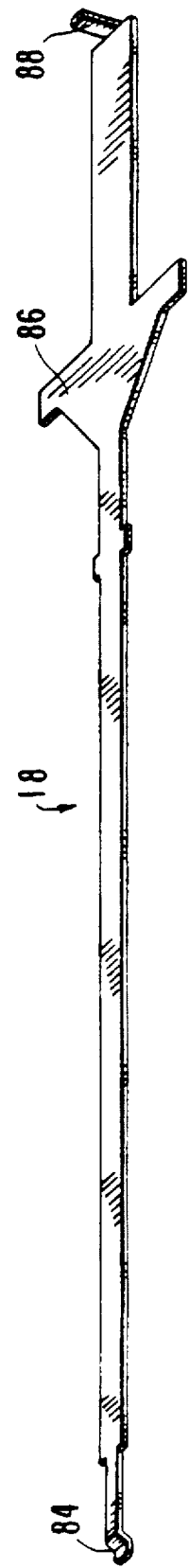

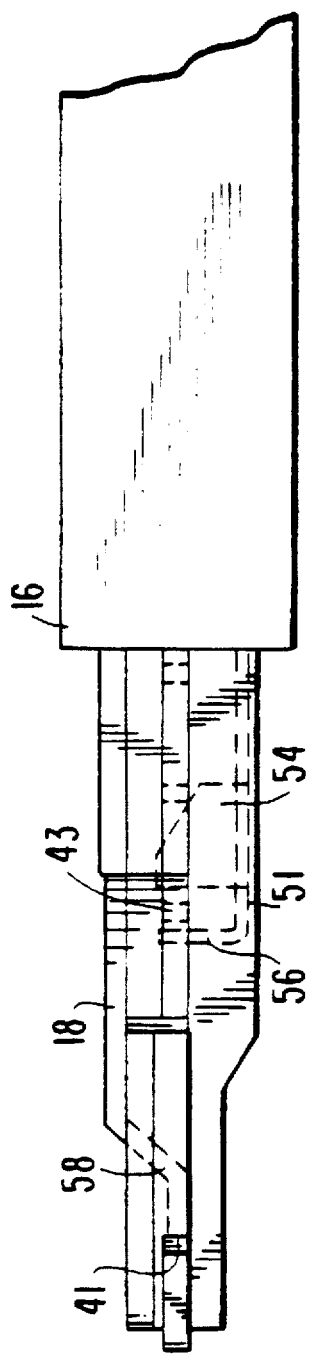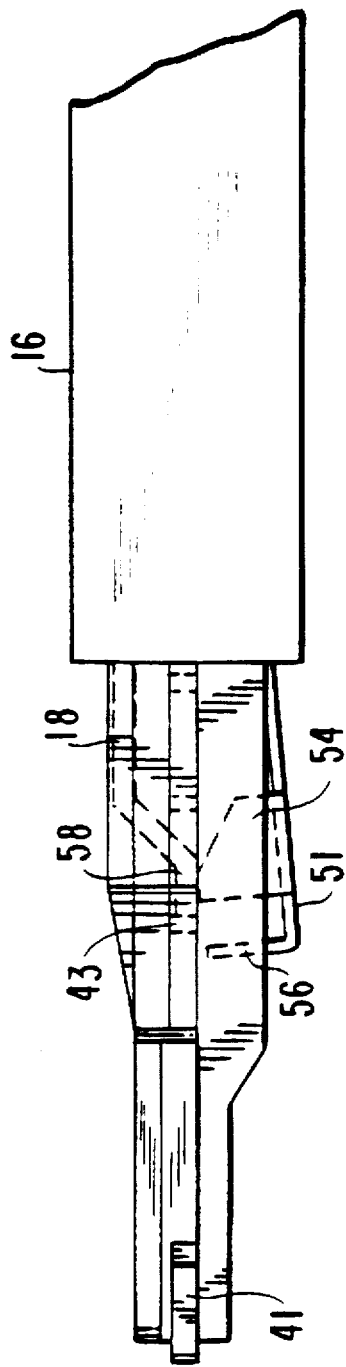

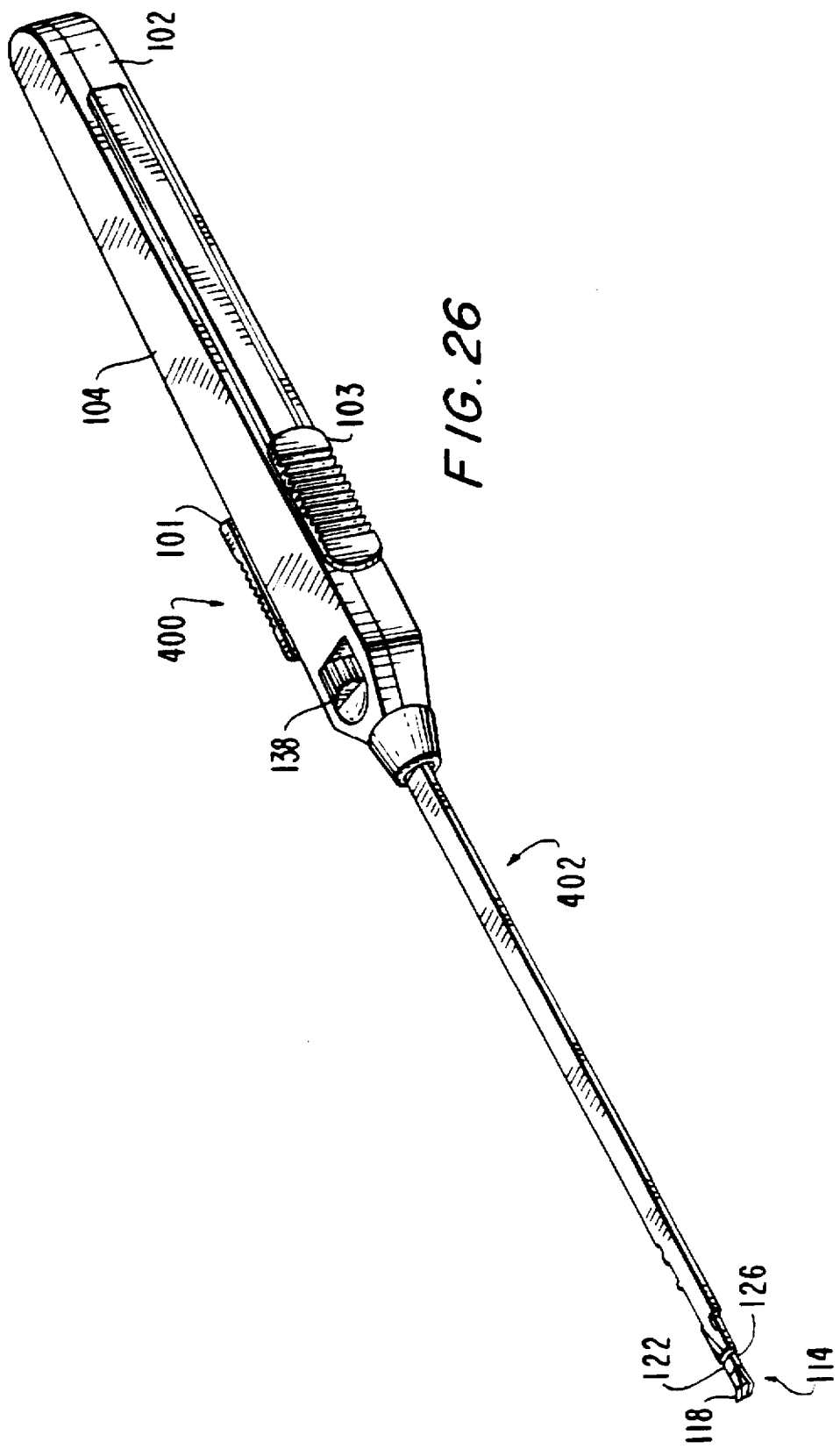

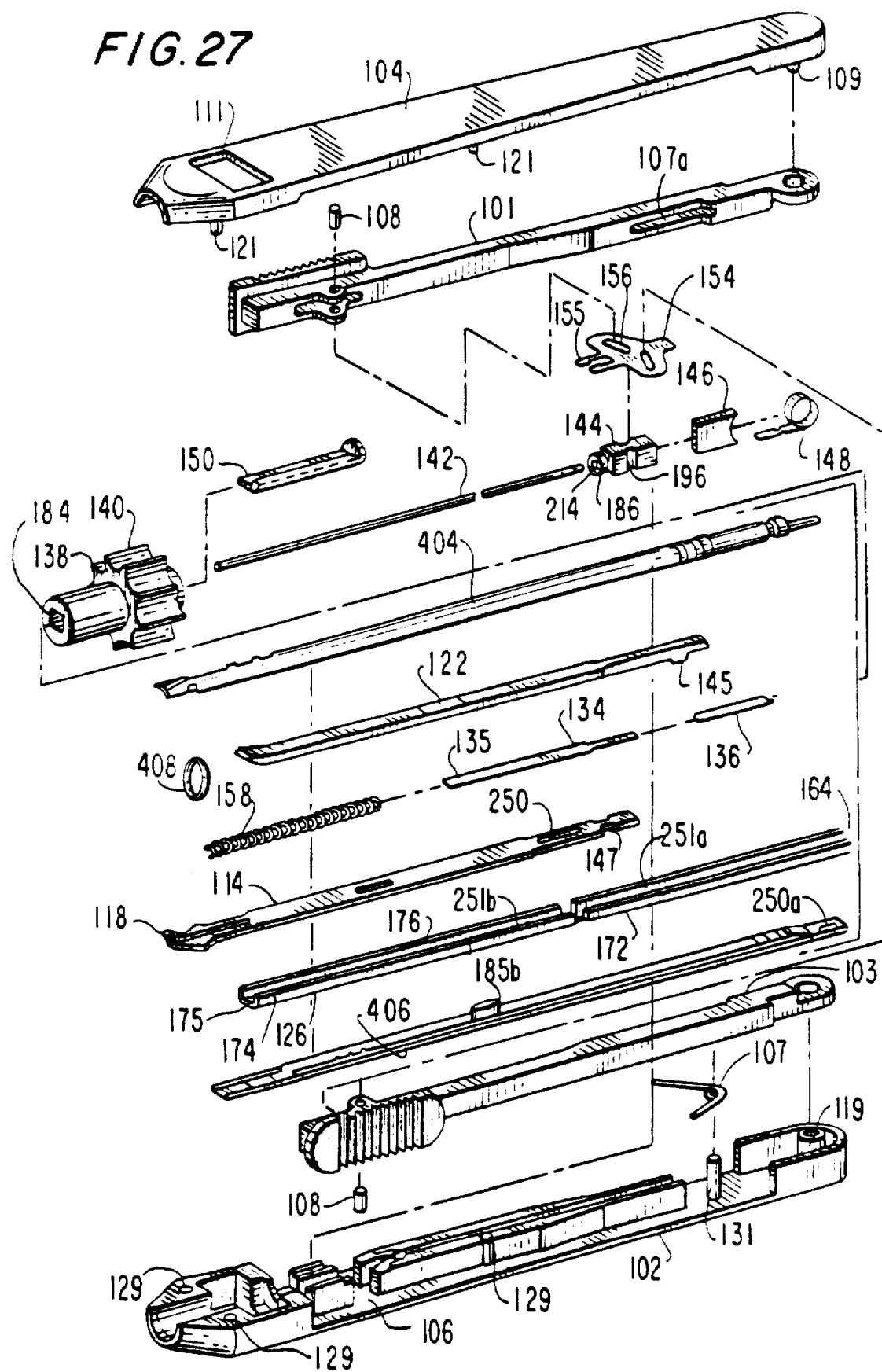

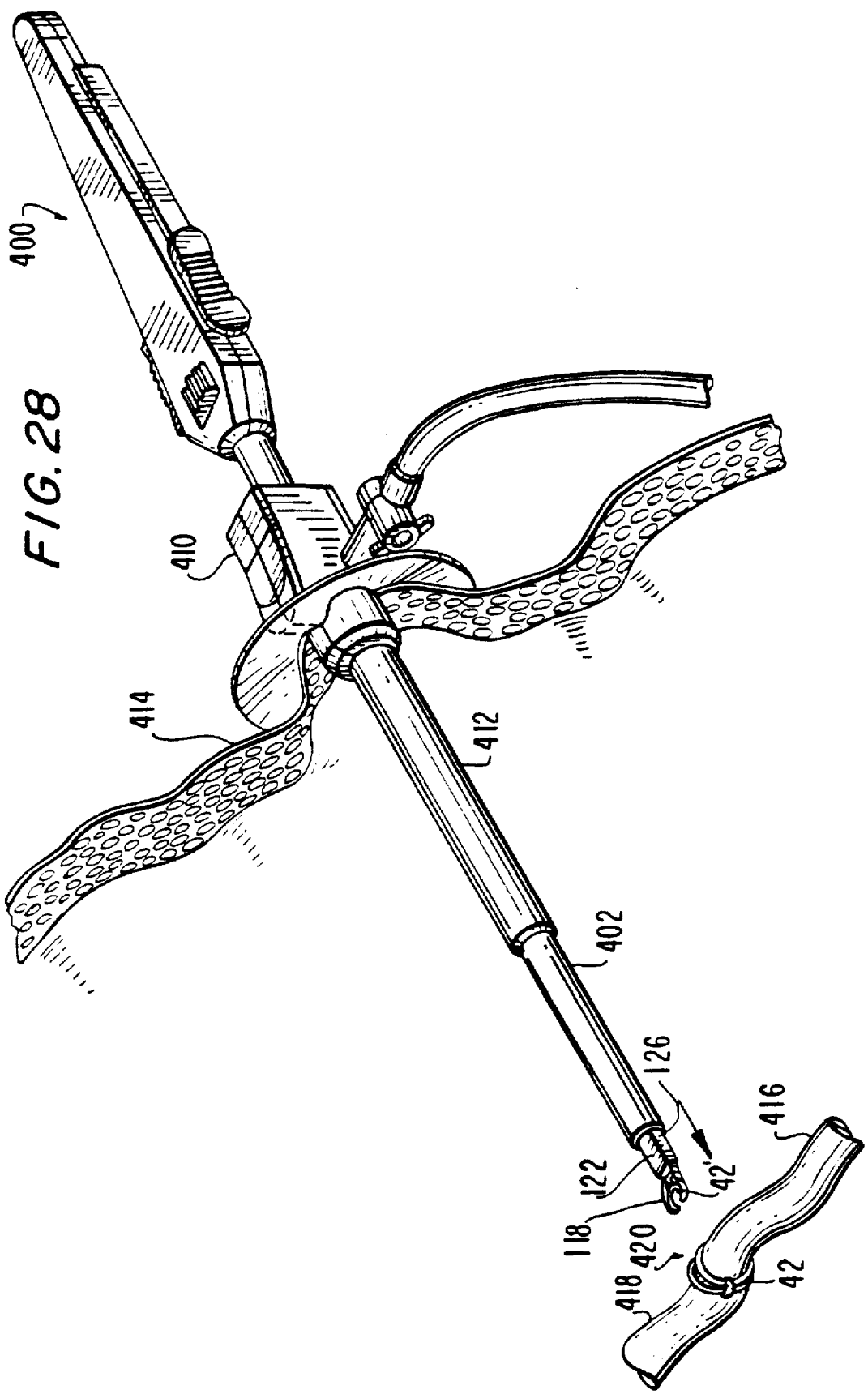

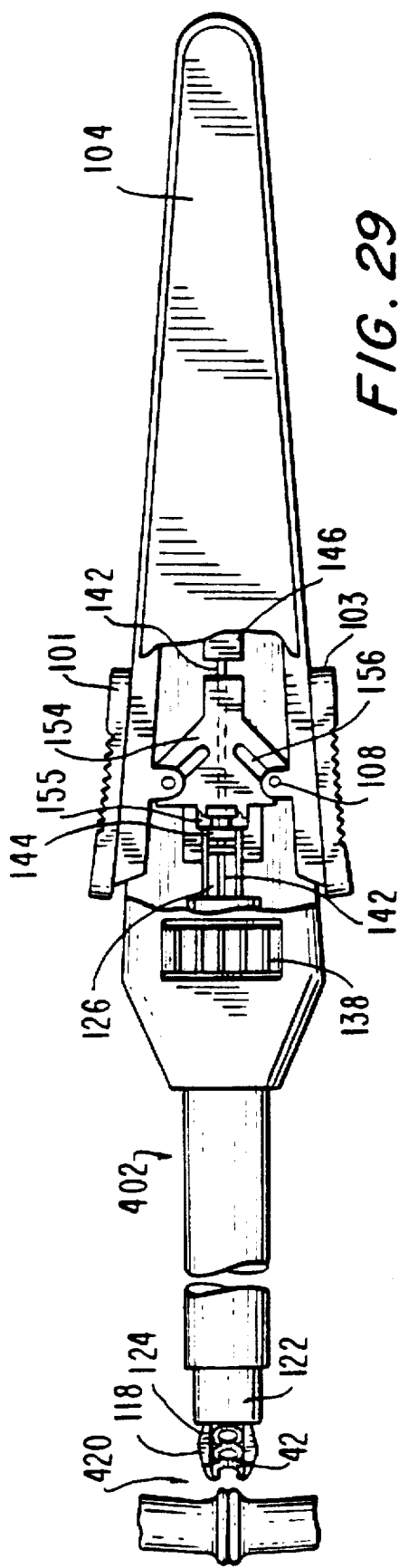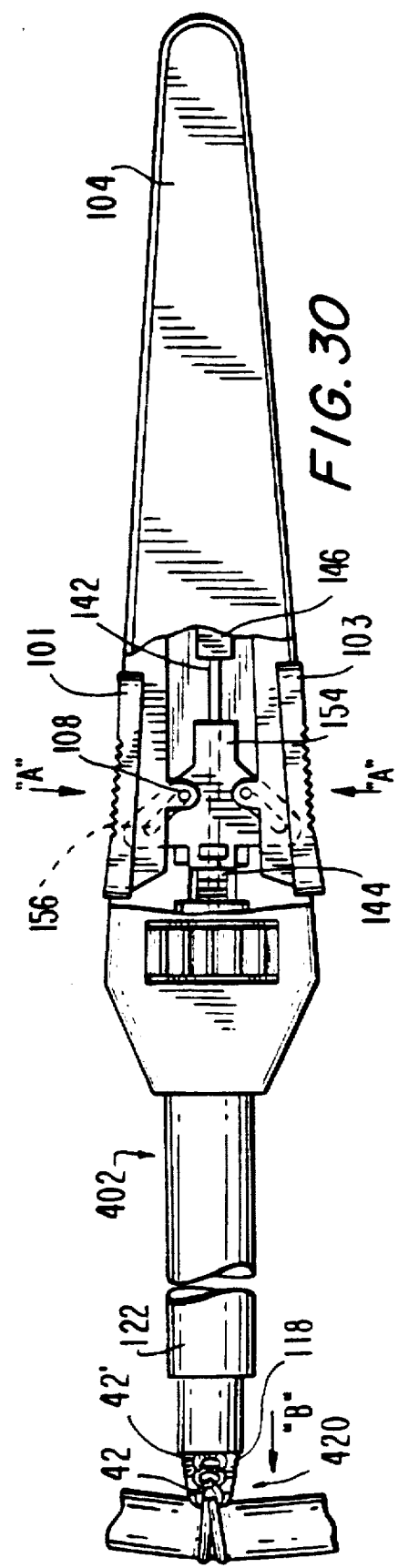

METHOD OF PERFORMING A VESSEL ANASTOMOSIS USING A SURGICAL CLIP APPLIER

CROSS-REFERENCE TO RELATED APPLICATIONS

This is a continuation, of Appln. Ser. No. 08/467,952 filed on Jun. 6, 1995, now abandoned, which is a continuation of Appln. Ser. No. 08/311,049, now abandoned, filed on Sep. 23, 1994, which is a continuation-in-part of Appln. Ser. No. 08/134,017 filed on Oct. 8, 1993, now abandoned which is a continuation-in-part of Appln. Ser. No. 07/959,201 filed on Oct. 9, 1992, now abandoned. The contents of these applications are incorporated herein by reference.

BACKGROUND OF THE INVENTION

1. Field of the Invention

This application relates to an instrument for applying to surgical clip to body tissue, and more particularly to instruments for applying a surgical clip for anastomoses of a blood vessel in conventional surgical procedures and endoscopic or laparoscopic surgical procedures.

2. Discussion of the Prior Art

The term "anastomosis" covers a variety of procedures in which blood vessels such as veins and arteries, or other tubular members, such as parts of the colon, intestines, stomach, etc., are joined or reconnected. These vessels may be joined in a variety of relative orientations, including end-to-end and end-to-side. Solid tubular structures such as peripheral nerves can also be joined together, as well as solid structures such as subcutaneous tissue and skin.

The recent advances made in the field of microsurgery has led to the development of alternatives to conventional suturing processes of joining vessels in order to accommodate the minute size of the vessels, nerves and tissues being joined during microsurgical procedures. These alternatives have also been developed with an eye towards preventing thrombosis which tends to occur at the points of penetration of the needle and sutures. An alternative to suturing is the use of surgical clips which are applied along the vessel juncture to perform a holding function similar to that of sutures, but without penetrating the vessel walls. Two such non-penetrating clips are shown in U.S. Pat. Nos. 4,586,503 and 4,733,664 to Kirsch et al. The former patent discloses a surgical microclip formed of plastically deformable metal or plastic material having minimal spring-back when crimped. The clip has a pair of parallel curved legs joined by a bridge at one end and terminating in rounded tips at the other end. The clip grips the edges of adjacent and everted tissue by crimping the legs together. The latter patent discloses a vascular surgical clip comprising a plastically deformable body portion, a tang for deforming the body, and a neck connecting the tang to the body, wherein the neck is designed to break upon application of a predetermined excessive tensile force to the tang, and the body is designed to deform upon application to the tang of less than the predetermined tensile force.

As described in the above patents, the non-penetrating clips are applied over opposed edges of the vessels, the edges first being everted, or turned outward, to form flanges that are gripped between the jaws of the clips. Eversion not only enables the clip jaws to better grip the vessels, but also insures that only the interior surfaces of the vessels are in contact.

Vascular microsurgical clips are typically applied with a small hand-held tool that enables the surgeon to precisely place the clip over the tissue edges, and then to close the clip, as by applying a squeezing pressure to the tool. One example of a prior art clip applier for use in vascular microsurgery is disclosed in both U.S. Pat. Nos. 4,733,664 and 4,929,240 to Kirsch et al. These patents disclose a tool for applying a surgical clip, the tool including means for gripping and applying tension to the tang of the clip while also having means for simultaneously pushing against shoulders on the clip body. The tool disclosed in these patents requires that a clip be reloaded into the clip applier after each clip is fired, which is disadvantageous in that the vessels being repaired need to be returned to their intended function as quickly as possible, particularly blood vessels. Furthermore, the devices disclosed in these patents and in the prior art generally require relatively large incisions for the surgeon to access the vessel to be repaired.

The development of laparoscopic and endoscopic surgical procedures and the success of these procedures has led to the need for microsurgical tools such as vascular clip appliers which can be utilized without requiring large incisions. Vascular clip appliers which apply microclips by accessing the surgical site through trocar cannulas would greatly benefit the patient through significantly reduced recovery time.

The need therefore exists for an instrument for applying such a surgical clip which can be utilized for vascular anastomosis, particularly during endoscopic and laparoscopic surgical procedures. One specific need is for an instrument that can hold a plurality of clips and automatically feed and apply the clips individually to the vessel. It would also be desirable for the instrument to include an elongated body portion which may be placed down a trocar cannula to access the surgical site in an endoscopic or laparoscopic surgical procedure. The instrument needs to be simple to manufacture, easy to manipulate and which applies the clips with consistent accuracy so as to provide a secure joining of vessels and tissue. Since the instrument is intended to apply clips during vascular anastomosis it would be desirable to configure it similarly to other vascular surgical devices, i.e. tweezers or pincer-like implements, which are held between the thumb and forefinger of the user.

SUMMARY OF THE INVENTION

The present application discloses an instrument for applying a surgical clip to a blood vessel during a microsurgical anastomosis procedure. The clip applier is designed for storage of multiple clips, and individual, automatic feed of the clips into the jaws of the instrument. Further, the applier is designed to be similar in design to other instruments used during vascular surgical procedures, i.e. to be like a tweezer or other pincer-like implement at the handle end, while also including an endoscopic portion to enable the instrument to be placed through a trocar cannula to access an internal surgical site during an endoscopic or laparoscopic surgical procedure.

The present device provides a surgical clip applier which is constructed with a pair of jaws for receiving and deforming a clip therebetween, a clip holding means having a series of clips for delivery to the jaws, a feed bar having a nose at a distal end and means for sequentially moving the feed bar from an initial distal-most position with the nose behind a clip positioned between the jaws to a proximal-most position behind a foremost clip of the clip series. A pusher bar moves the series of clips distally. Alternately, the series of clips may be arranged for a sequential feed to the jaws under spring biasing, so that the feed bar may be eliminated.

The means for sequentially moving the feed bar includes a pair of handles which are connected to the feed bar and which are movable between an open position corresponding to the distal-most position of the nose and a closed position corresponding to the proximal-most position of the nose. The handles also effect the closing of the jaws to crimp the clip positioned in the jaws, by advancing a channel assembly during closing of the handles which cams the jaws shut. The handles are oppositely and pivotally connected at the proximal end of the housing and are actuated at their distal ends, thereby improving the tactility and visibility of the working end of applier, as well as the stability of the instrument.

The jaws are part of a jaw blade assembly which is fixedly connected to the housing. The channel assembly is slidably mounted with respect to the housing to envelop the jaw blade assembly with the feed bar slidably mounted in the channel assembly in overlying relation to the clip holding means. A spring is provided in the housing for biasing the feed bar in a distal direction and for biasing the channel assembly in a proximal direction such that the handles are also biased into an opened position. A clip retainer is provided to prevent movement of the clips by holding the clips against movement of a pusher bar which moves the series of clips positioned on the clip holding means, until the feed bar moves proximally and biases the clip retainer away from the series of clips so that the pusher bar may move the series distally as the feed bar slides the next clip between the jaws.

In operation, the applier initially has a clip positioned between the jaws. Thus, a surgeon places the jaws of the applier about the everted end of the vessels and then squeezes the handles together. In response to closing of the handles the channel assembly is moved in a distal direction thereby closing the jaws to crimp the clip. At the same time, the feed bar is moved in a proximal direction to a position behind the foremost clip in the clip holding means. Once the handles are released, the jaws open to release the crimped clip, and the feed bar moves in the distal direction to push the foremost clip in the series to a position between the jaws. The applier is then ready for application of the next clip.

In another embodiment, the clip applier includes a rotation knob for rotating the channel, jaw blade assembly, clip cover and a feed mechanism which is independent of the handle. This clip applier also includes a window for viewing a clip indicator which displays approximately how many clips remain in the device. Further, the tip of the jaws are angled approximately 30 degrees for better visibility during application of the clip. In this embodiment, a spring biased pusher bar is located behind the series of clips and urges the series forward in the distal direction towards the jaws. The jaws include a raised stop portion having an arcuate clip receiving groove which arrests forward or distal movement of the clips and accurately positions the next clip in the jaws for crimping. After the handles are closed to crimp the clip in the jaws, and then are opened to release the crimped clip, the pusher bar urges the series distally to place the next clip in between the jaws.

In yet another embodiment, the clip applier includes an elongated portion for insertion through a trocar to perform endoscopic and laparoscopic procedures. A seal may also be provided to prevent inadvertent leakage of the insufflation gas utilized in such procedures. The seal may comprise an O-ring or similar type seal to prevent leakage through the instrument itself. The instrument permits the application of microclips in endoscopic procedures to repair vessels without large incisions.

BRIEF DESCRIPTION OF THE DRAWINGS

The present application will be more fully appreciated as the same becomes better understood from the following detailed description of the present invention when considered in connection with the following drawings in which:

FIG. 8 shows an enlarged perspective view of the clip cover of the instrument;

FIG. 9 shows an enlarged perspective view of the jaw blade assembly and clip retainer of the instrument;

FIG. 10 shows an enlarged perspective view of the pusher bar of the instrument;

FIG. 11 shows an enlarged perspective view of the feed bar of the instrument;

FIG. 12 shows a side view of the distal end of the instrument illustrating an unformed clip positioned in the jaws of the instrument;

FIG. 13 shows a side view of the distal end of the instrument illustrating the position of the clip retainer and feed bar after the clip has been formed in the jaws;

FIG. 26 illustrates a perspective view of another embodiment of the instrument particularly useful for endoscopic procedures;

FIG. 27 illustrates an exploded perspective view of the instrument of FIG. 26;

FIG. 28 illustrates a perspective view of the instrument during an endoscopic surgical procedure in which the instrument is placed through the body wall through the provision of a trocar cannula;

FIG. 29 illustrates a top plan view in partial cross-section illustrating the operating mechanism of the instrument prior to crimping a clip positioned in the jaw assembly; and FIG. 30 is a view similar to FIG. 29 illustrating the operating mechanism of the instrument as a clip is being crimped in the jaw assembly and applied to the vessel.

DETAILED DESCRIPTION OF THE PREFERRED EMBODIMENT

Figure 1:
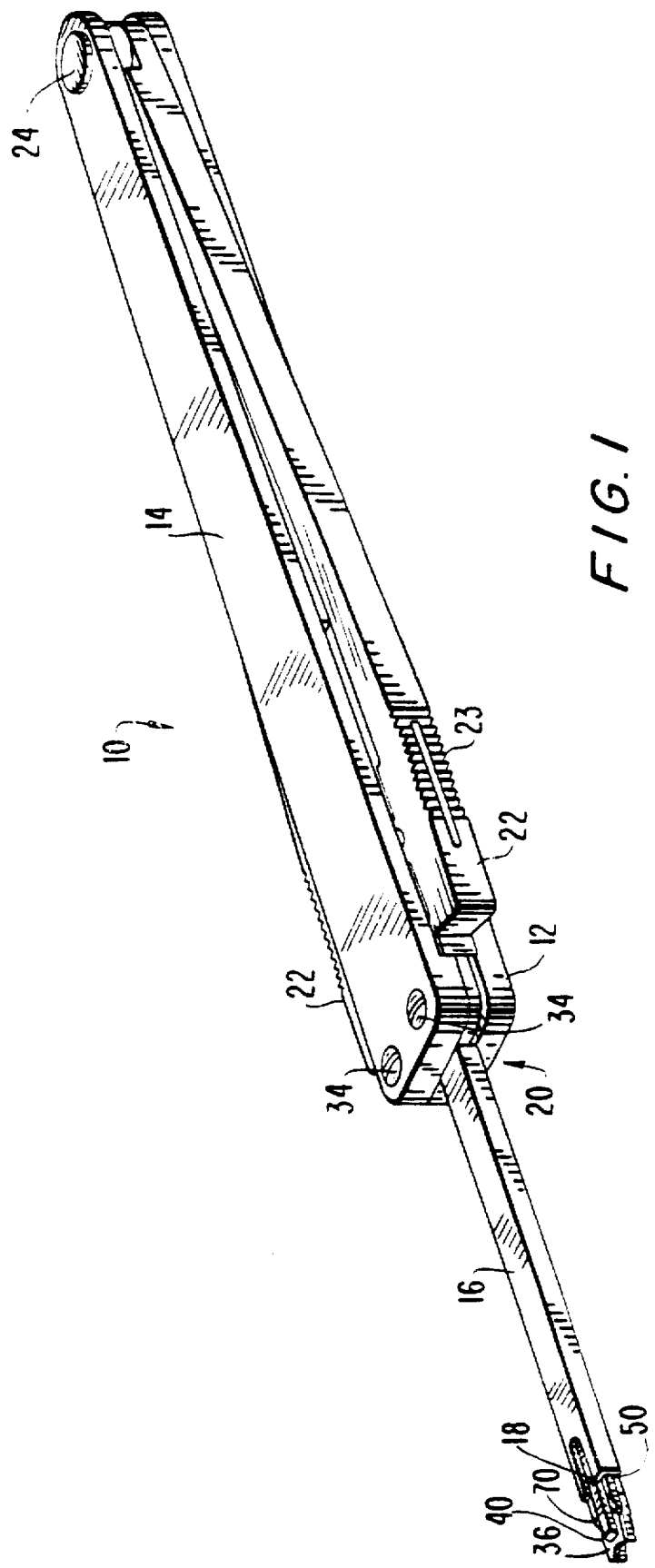
FIG. 1 illustrates a perspective view of a first embodiment of the instrument.
Figure 2:
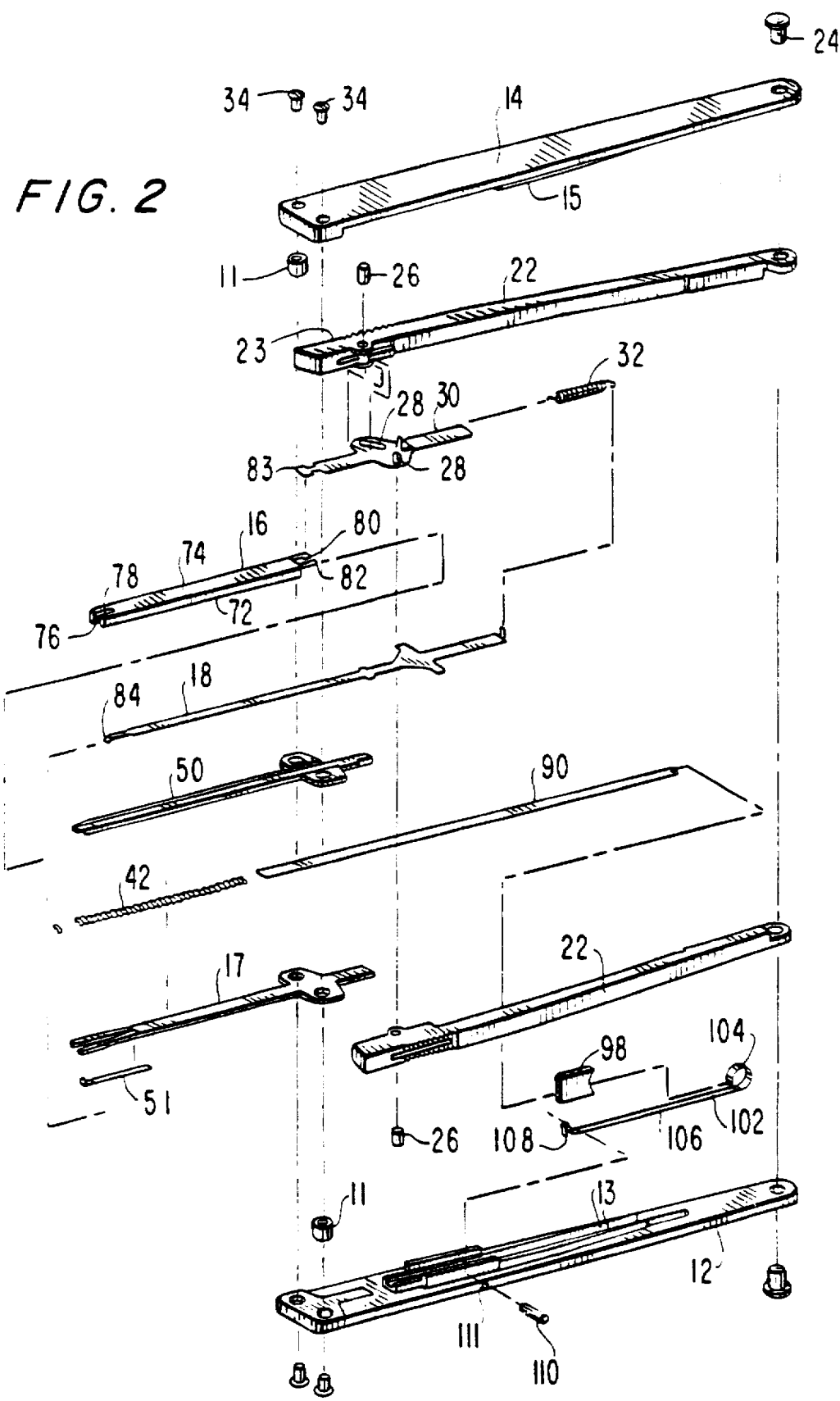
FIG. 2 illustrates an exploded perspective view of the instrument.

Referring now to drawings, in which like reference numerals identify similar or identical elements throughout the several views, and referring in particular to FIGS. 1 and 2, the surgical clip applier 10 of the present invention includes a bottom housing 12, a top housing 14, a jaw blade assembly 17 having a pair of jaws, a channel assembly 16 slidably mounted with respect to housings 12, 14, a clip cover 50 and a feed bar 18 slidably mounted in the channel assembly 16. A pair of handles 22 are provided for actuating the clip applier and are pivotably secured to housings 12 and 14 as described below.

Figure 3:
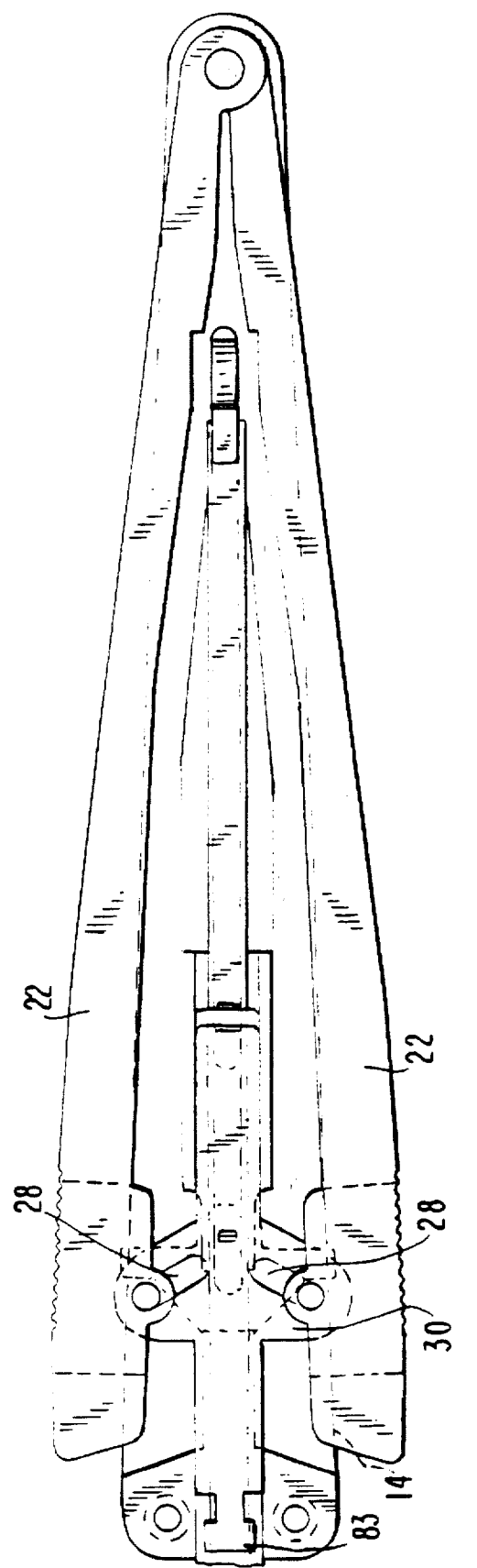
FIG. 3 illustrates a top view of the handle of the instrument taken along lines 3—3 of FIG. 1.

Bottom and top housings 12, 14 are secured together by pivot pin 24 and screws 34. The housings 12, 14 are of slender construction and are made of any suitable material, for example, plastic material. As seen in FIG. 2, the inner surface 13 of the bottom housing 12 is contoured and recessed so as to receive various components of the applier as further explained below. The inner surface 15 of top housing 14 is contoured for similar purposes. The pivot pin 24 extends through the proximal end of the housings 12, 14 and the proximal end of handles 22, as best seen in FIG. 3, to pivotally connect the handles 22 between the inner surfaces of the housings 12, 14 which are spaced apart to form a recess for receiving the handles 22. Spacers 11 are positioned in the housings 12, 14 to help maintain the recess between the housings 12, 14.

As shown in FIG. 1, the handles 22 are actuable at their distal ends 23, i.e. the end closest to the surgical site. This provides increased visibility, tactility and stability and enables the handles 22 to be held in a tweezer or pincers like manner.

Figure 7:
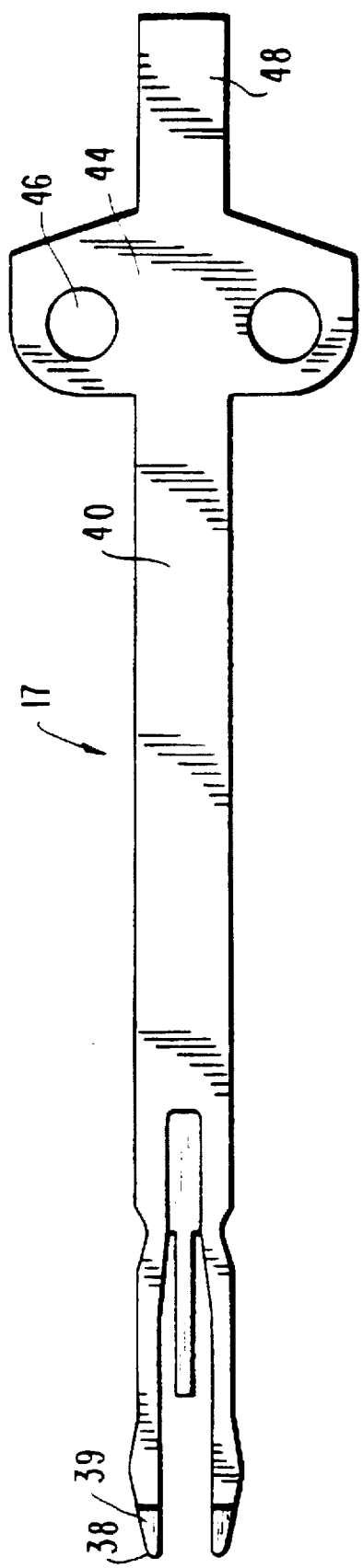
FIG. 7 shows an enlarged top view of the jaw blade assembly of the instrument.

Turning now to the jaw blade assembly 17 for forming the clip and with reference to FIGS. 2, 7 and 9, jaw blade assembly 17 includes an elongated jaw blade 36 which has a pair of jaws 38 formed at a bifurcated distal end for receiving a surgical clip therein. Each jaw 38 is provided with a small slot or groove in a side wall so as to receive therein a leg of the substantially C-shaped surgical clip 42 shown in FIGS. 14 and 15. Each jaw 38 also includes raised portions 39 which act as a stop for the clip cover 50 mounted thereon. The jaw blade 36 has a pair of camming surfaces 41 for engagement by channel assembly 16 to close the jaw in a manner described below.

The jaw blade assembly 17 also includes along its elongated portion a clip carrier portion 40 upon which a series of clips 42 are positioned. In this embodiment the clip carrier portion 40 is integral with the jaw blade assembly 17, although multiple elements could be used to achieve the same result.

The proximal, or rear, end of the jaw blade assembly 17 includes a plate 44 having a pair of oppositely positioned openings 46 for receiving the screws 34 which retain the jaw blade assembly 17 within the housings 12, 14. A tail 48 is formed in the proximal-most end of the jaw blade assembly 17 for providing additional support for the pusher bar 90.

A clip retainer 51 is mounted under the distal end of jaw blade assembly 17. With reference to FIGS. 9, 12 and 13, the distal end of the clip retainer 51 has a pair of oppositely positioned side walls 52 and 54 and a raised distal end wall 56. The clip retainer 51 prevents movement in the distal direction of the stack of clips 42 and is movable from a position preventing movement of stack of clips 42, as shown in FIG. 12, to a position in which the stack of clips 42 are able to advance distally, as shown in FIG. 13.

As shown in FIGS. 2 and 11–13, the feed bar 18 is elongated and has a depending nose 84 at its distal end. Nose 84 moves clip retainer 51 into the position shown in FIG. 13 by engagement of the walls 52 and 54 when the feed bar 18 has moved behind a second clip 43 in the series of clips 42, but the first clip 42' is still in the jaws 38 of the jaw assembly.

As indicated, the distal end of the feed bar 18 is angled slightly downwardly with the tip bent up. Feed bar 18 functions to feed the distal-most clip in the series of clips to the jaws and is slidably positioned within channel 64 between rails 66 (see FIG. 8) of the clip cover 50. Feed bar 18 further includes a pair of triangular projections 86 having cam surfaces 87 which cam the feed bar 18 in the proximal direction when the handles 22 are closed, and a proximal abutment 88 for receiving spring 32 as mentioned below.

Clip cover 50, shown in FIGS. 2 and 8, is elongated and similar in shape to the jaw blade assembly 17 and includes a tissue stop 70. The tissue stop 70 extends distally over the jaw blade 36. This tissue stop 70 has a bifurcated distal end which overlies and serves as a guide to prevent tissue from impeding movement of the clip 42' into the jaws 38. The tissue stop 70 has a rounded cut out 53, a slot 60 and a pair of rounded ends 62 at its distal end. Slot 60 is provided for enabling nose 84 of feed bar 18 to access the series of clips 42 to feed clips to the jaws 38. The pair of side walls or rails 66 provide a guide channel 64 for the feed bar 18. The bottom surface 69 of the clip cover 50 is positioned atop jaw blade assembly 17 and includes a pair of downwardly extending side walls or rails 67 between which the series of clips 42 and the pusher bar 90 (see FIGS. 2 and 10) are provided.

Referring again to FIGS. 1 and 2, the channel assembly 16, which as mentioned above functions to cam jaws 38 closed, defines an elongated channel shaped member for enveloping the jaw blade assembly 17 and includes a pair of upstanding walls 72, a top wall 74 and a bottom wall 76. The top wall 74 and bottom wall 76 include a cutout 78 at their distal ends, and at the proximal end top wall 74 includes recess 80 which is formed between projections 82. The projections 82 form a female dovetail connector which engages a male dovetail connector 83 of the forming cam 30 and thereby causes movement of the channel assembly 16 upon movement of the forming cam 30, as will be described below.

With reference to FIGS. 2 and 10, elongated pusher bar 90 has oppositely positioned projections 92 and a rounded member 94 extending from its distal end corresponding in shape to the bridge portion of the clips, for engaging and pushing the last and most proximal clip 42" (see FIG. 4) in the series of clips 42 on the clip carrier portion 40. The projections 92 engage the grooves 208 and the rounded member 94 engages the bridge portion 206 of the last clip 42". The proximal end of the pusher bar 90 includes a slot 96 for receiving a spring guide block 98. A coil spring 302 fits within the molded contours of bottom housing 12, and a channel 308 of spring 302 is engaged by the pin 310 which extends through an aperture 311 in the bottom housing 12 to hold the end of spring 302 in place as coiled portion 304 rolls in the distal direction, urging guide block 98 against pusher bar 90. This gently urges the series of clips 42 in the distal direction to continue the feeding, loading and clipping process. The feed spring 302 rolls along the top of its elongated portion 306 as the pusher bar 90 advances the clips 42.

Figure 14:
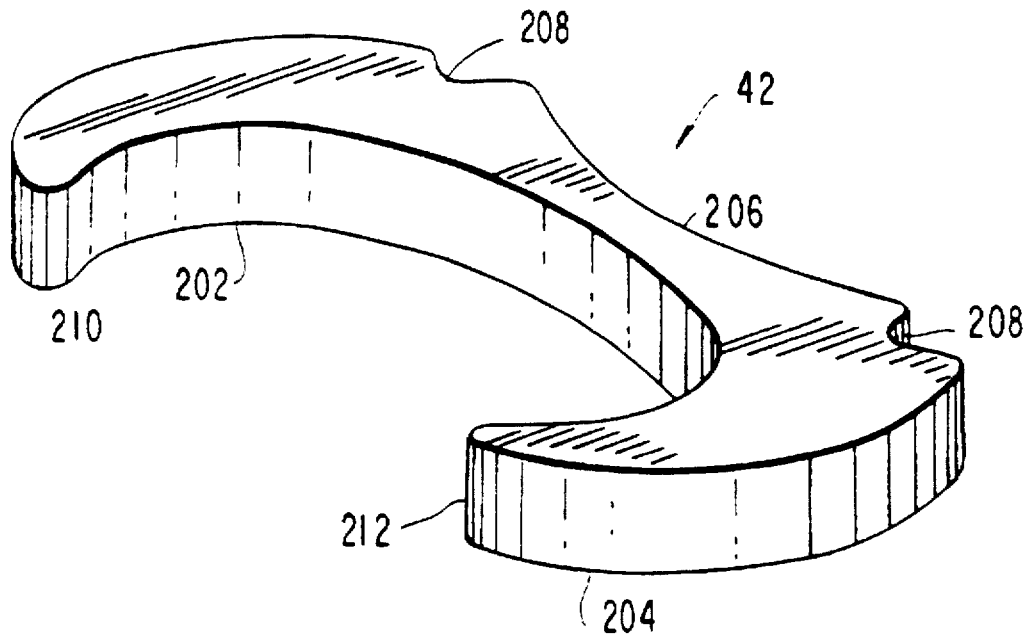
FIG. 14 shows an enlarged perspective view of a clip for use with the instrument.
Figure 15:
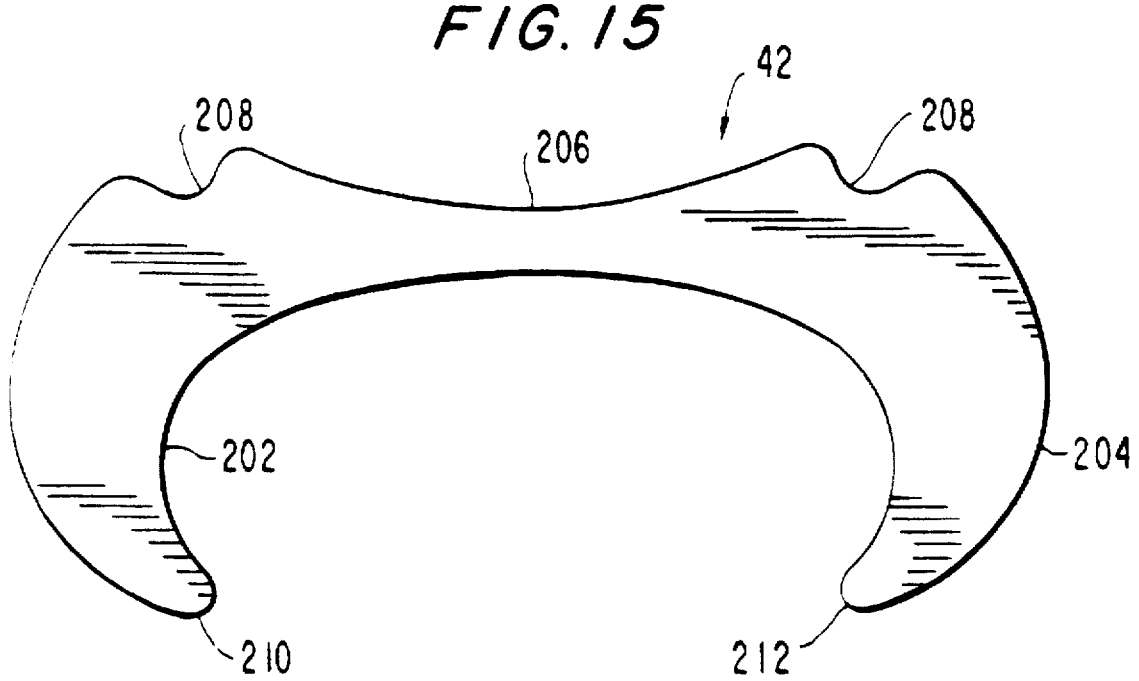
FIG. 15 shows an enlarged top view of the clip of FIG. 14.

As shown in FIGS. 14 and 15, a surgical clip designed for application by the clip applier 10 is formed of a unitary piece of biologically acceptable, plastically deformable material such as a noble metal (i.e. gold, silver, platinum, titanium etc.). While metal clips are presently preferred, it is contemplated that the other materials such as suitable polymer plastics may be used. The material, preferably titanium, is sufficiently ductile or plastically deformable so that when the clips are crimped there is minimal spring-back. The clip is designed to apply contact force to the tissue regardless of tissue thickness without penetration.

The clip 42 includes a pair of inwardly curved arms 202 and 204 interconnected by a bridge portion 206, the two arms extending generally perpendicular to the bridge portion 206. The arms terminate at tips 210 and 212 which are rounded to prevent injury to the subject tissue. As described above, the bridge portion 206 includes a pair of grooves 208 for engagement by the pusher bar 90 of the clip applier 10 described above and for advancing the clips down the clip carrier 40 in the applier. The clip is sized according to the particular end use, but is generally of a size suitable for microsurgical applications, in both non-endoscopic and endoscopic procedures.

Turning now to the operation of the instrument, and referring to FIGS. 1, 2 and 3, each handle 22 is articulated to the housings 12 and 14, and is operable to effect movement of the channel assembly 16, the feed bar 18, and ultimately the series of clips 42 and the pusher bar 90 in the following manner. Handles 22 are pivotally connected to the housings 12, 14, by pivot pin 24 and extend from the housing on opposite sides as shown. The distal ends of handles 22 are secured by pins 26 which ride along cam slots 28 of forming cam 30. The forming cam 30 is connected at its distal end through the dovetail connection 82, 83 to the channel assembly 16, as is discussed in detail above, and near its proximal end post 29 is connected to a spring 32. The other end of the spring is attached to the proximal end of the feed bar 18 at abutment 88 and biases feed bar 18 in a distal direction. Thus, the spring 32 biases the channel assembly 16 and the forming cam 30 in a proximal direction, such that the handles 22 are biased to an open position, while at the same time biasing feed bar 18 in a distal direction.

Since each handle is connected in a similar fashion, only the connection of one of the handles will be discussed. As indicated in FIGS. 2 and 3, the channel assembly 16 is mounted at the distal end of forming cam 30 at dovetail connection 82, 83 while the feed bar 18 is attached at abutment 88 through spring 32 to the post 29 at proximal end of forming cam 30. Thus, referring to FIG. 3, when handles 22 close together, the pins 26 move along slots 28 of forming cam 30 to distally advance the forming cam 30 which correspondingly advances the channel assembly 16 against the biasing of spring 32. As seen in phantom in FIG. 3, feed bar 18 underlies forming cam 30 and is positioned such that cam surfaces 87 abut pins 26 as shown. As handles 22 are closed, pins 26 also ride over cam surfaces 87, thus moving feed bar 18 in a proximal direction and further extending spring 32, which is concurrently being pulled in the distal direction by forming cam 30. After the channel assembly 16 advances a slight distance distally, e.g. approximately 0.020 inch, the nose 84 of the feed bar 18 moves proximally to a position behind the next clip 43 in the clip carrier 40, as seen in FIG. 13.

Figure 4:
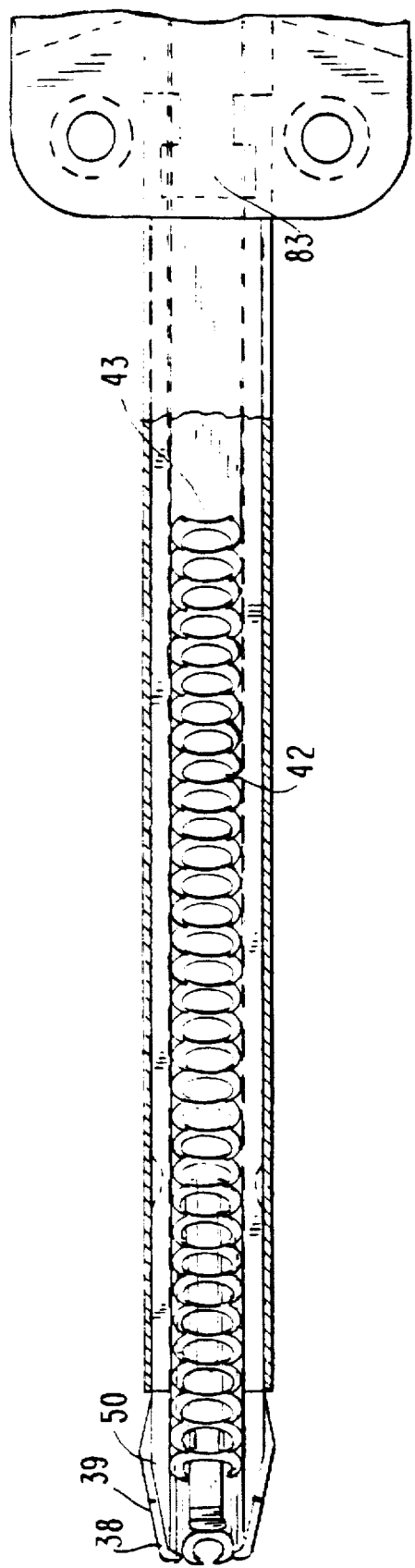
FIG. 4 shows a bottom view in partial cross-section of the distal portion of the instrument.
Figure 5:
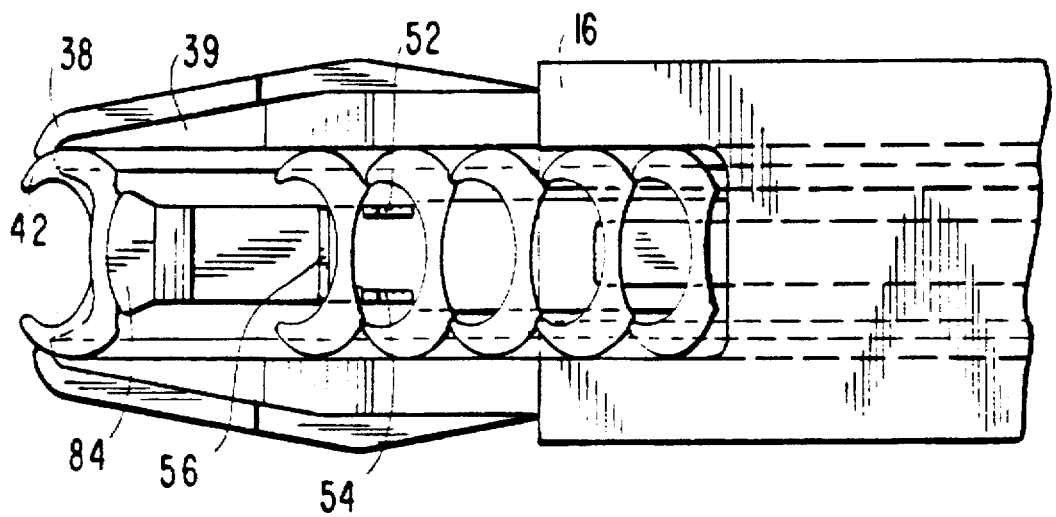
FIG. 5 shows a detailed top view of a unformed clip loaded in the jaws of the instrument.
Figure 6:
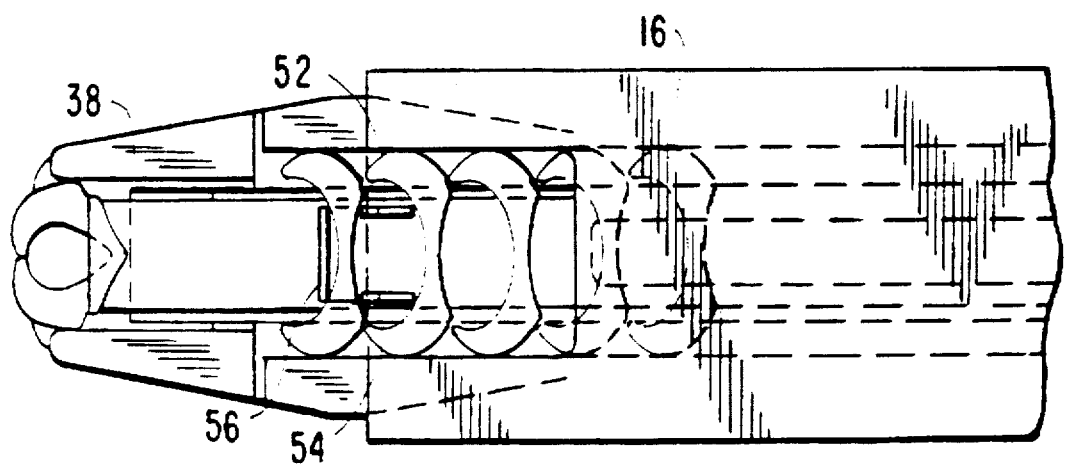
FIG. 6 shows a detailed top view of a clip being formed in the jaws of the instrument.

In use, the clip applier 10 is provided with a clip 42' already in the jaws 38 of the jaw blade assembly 17, and feed bar 18 is in the position shown in FIGS. 4 and 5 to hold clip 42 in place as it is fit over a vessel. To apply the clip, the handles 22 are first squeezed together overcoming the bias of spring 32 and causing the channel assembly 16 and forming cam 30 to move forwardly (or distally), while at the same time, the teed bar 18 moves rearwardly (or proximally) as pins 26 engage cam surfaces 87, into a position to feed the second clip 43 from the series of clips 42 on clip carrier 40 as described above. As the channel assembly 16 moves forwardly and over jaws 38 of the jaw blade assembly 17, the jaws 38 are cammed closed to form the clip 42' therein, as seen in FIG. 6. As the jaws 38 close and feed bar 18 moves proximally, the nose 84 of the feed bar 18 moves behind the second clip 43, as seen in FIG. 6, and the first clip 42' is fully formed in the jaws 38. The clip retainer 51, as seen in FIGS. 12 and 13, then is biased downwardly by engagement with the nose 84 of feed bar 18.

As the handles are released, handles 22 automatically open under the influence of spring 32, which pulls forming cam 30 proximally and pushes feed bar 18 distally causing pins 26 to ride in slots 28 to open handles 22. The clip retainer 51 continues to be biased downwardly, and the feed cam 18 moves forward and advances the next clip 43 to the jaws 36, due to pins 26 riding over cam surfaces 87 as spring 32 biases feed bar 18 in the distal direction. Furthermore, as pins 26 ride in slots 28 of forming cam 30, cam 30 moves proximally under the influence of spring 32, drawing channel assembly 16 with it. The downward biasing of the clip retainer 51 also permits the stack of clips 42, which are normally biased in a forward direction by spring 302, to advance forward and move distally, to position the next distalmost clip in position for loading after the crimping of clip 43.

Figure 16:
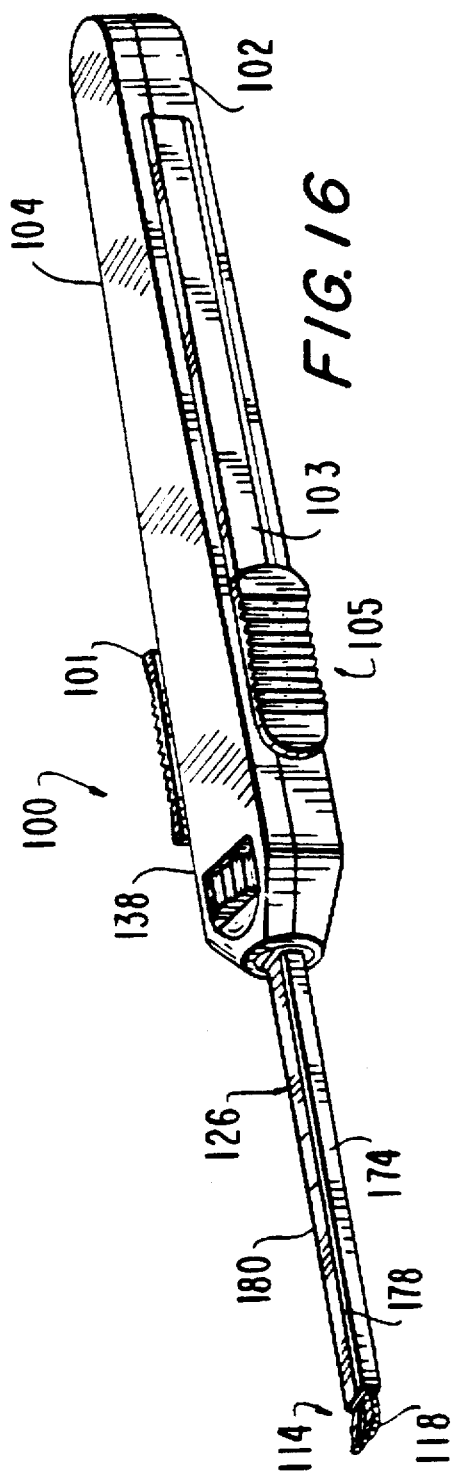
FIG. 16 is a perspective view of another embodiment of the instrument.

Referring now to FIG. 16, the surgical clip applier 100 of an alternative embodiment of the present applier includes a bottom housing 102, a top housing 104, a jaw blade assembly 114 having a pair of jaws 118, and a channel assembly 126 slidably mounted with respect to housings 102, 104. A pair of handles are provided for actuating the clip applier and are pivotably secured to housings 102 and 104.

The bottom and top housings 102, 104 are press fit and held together by the engagement of pin 109 with the pin receiver 119 and by the engagement of pins 121 with holes 129, but alternatively may be welded or joined by other suitable means. The housings 102, 104 are of slender construction are made of any suitable material, for example, plastic material. As indicated, the inner surface 106 of the bottom housing 102 is contoured and recessed so as to receive various components of the applier as further explained below. The inner surface 106 of top housing 104 is contoured for similar purposes. The pivot pin 109 extends from the proximal end of the housing 104 to pivotally connect the handles 101, 103 between the inner surfaces of the housings 102, 104, which are spaced apart to form a recess for receiving the handles 101, 103. The housing 104 also includes a window 111 through which the knob 138 extends as seen in FIG. 16.

The handles 101, 103 are actuable at their distal ends 105, i.e. the end closest to the surgical site. This provides increased visibility, tactility and stability and enables the handles 101, 103 to be held in a tweezer or pincer-like manner. The handles 101, 103 are biased outwardly by a spring 107 which fits in slots 107a of each handle member and is retained by the spring post 131 formed on the inner surface 106 of the bottom housing 102.

Figure 18:
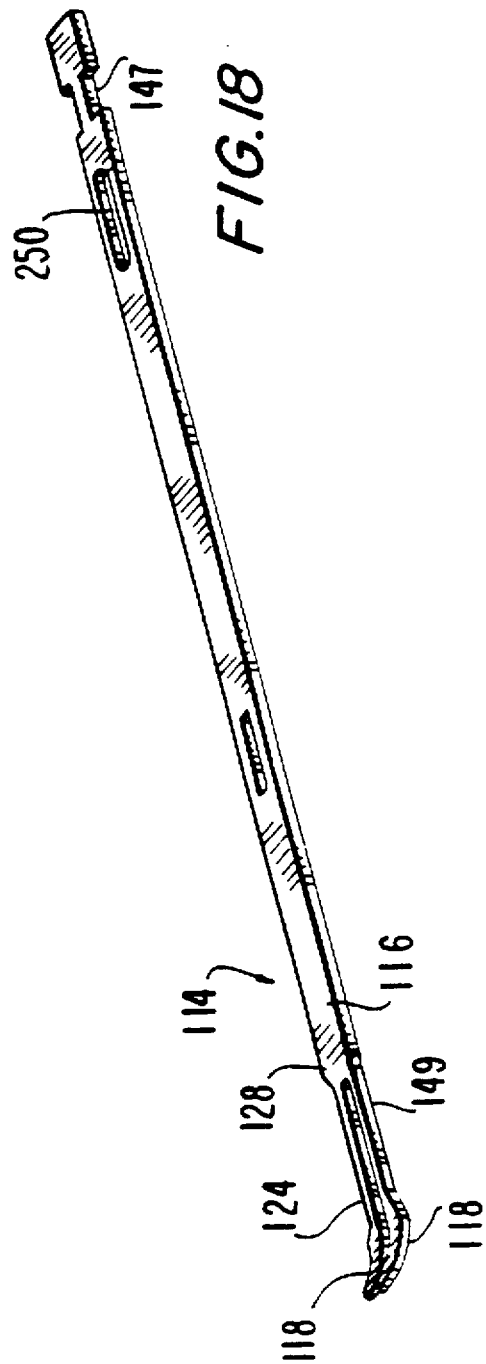
FIG. 18 is an enlarged perspective view of the jaw blade assembly of FIG. 17.
Figure 17:
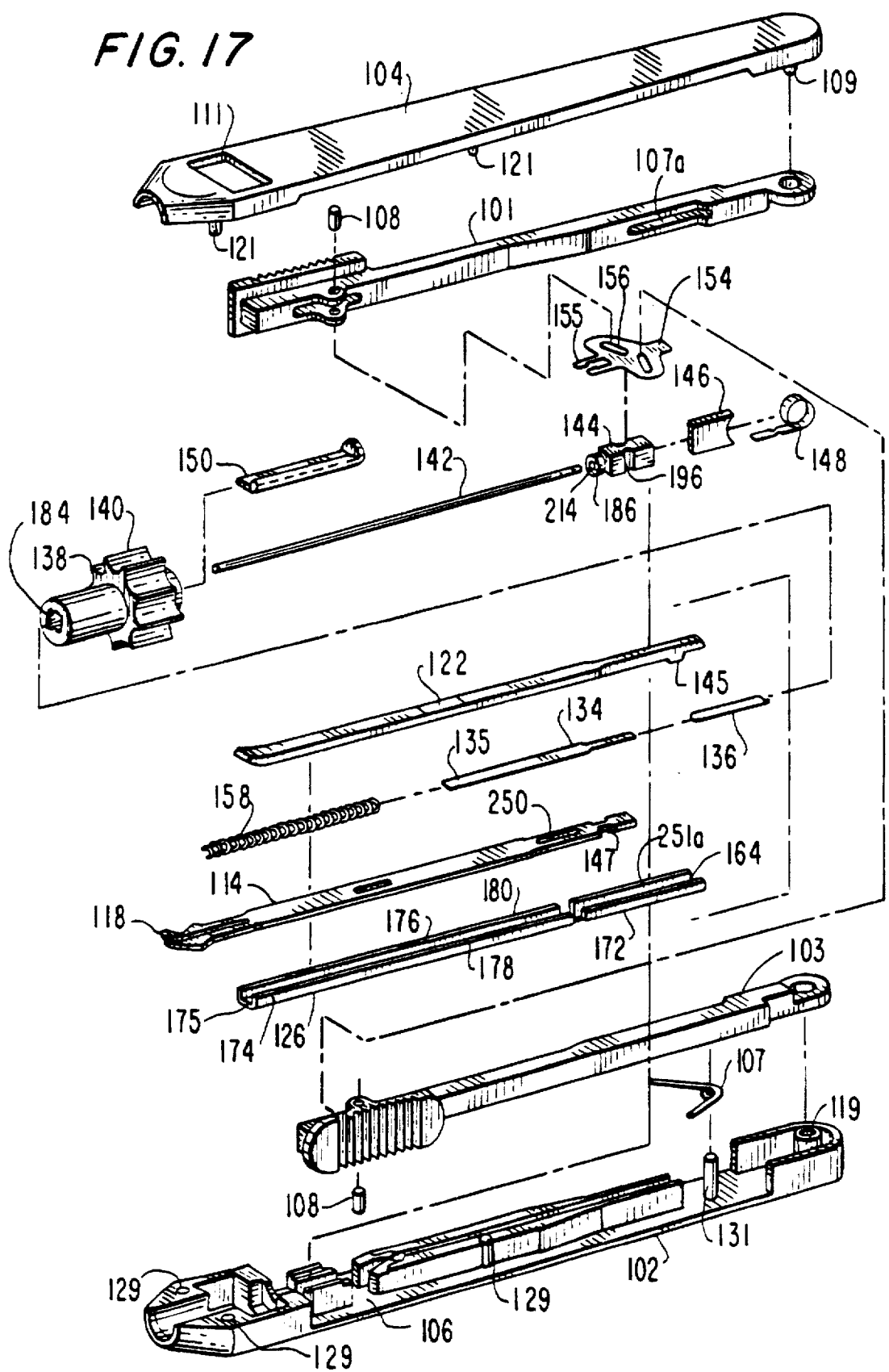
FIG. 17 is an exploded perspective view of the instrument of FIG. 16.
Figure 23:
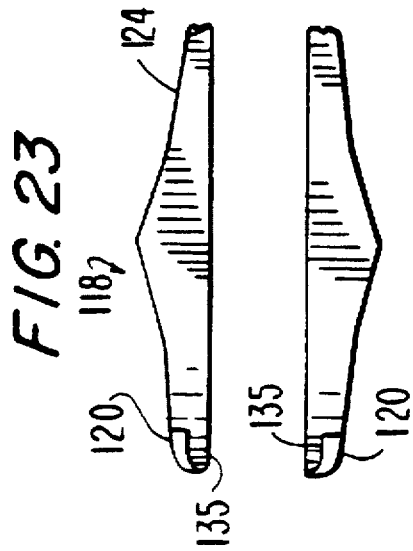
FIG. 23 is an enlarged, partial top view of the distal end of the jaw blade assembly of FIG. 18.
Figure 24:
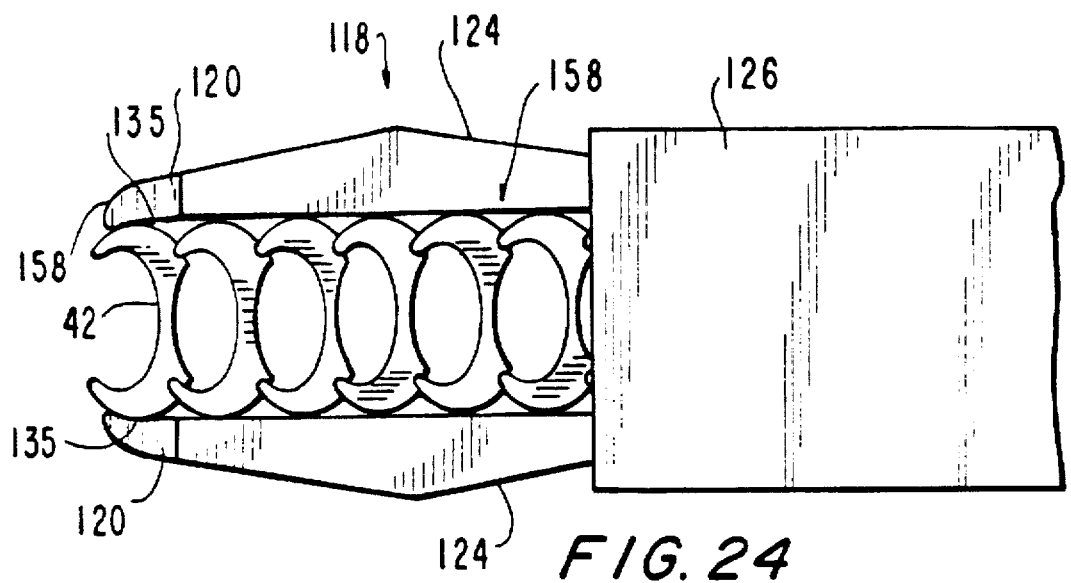
FIG. 24 shows a detailed top view of an unformed clip loaded in the jaws of the instrument of FIG. 17.
Figure 25:
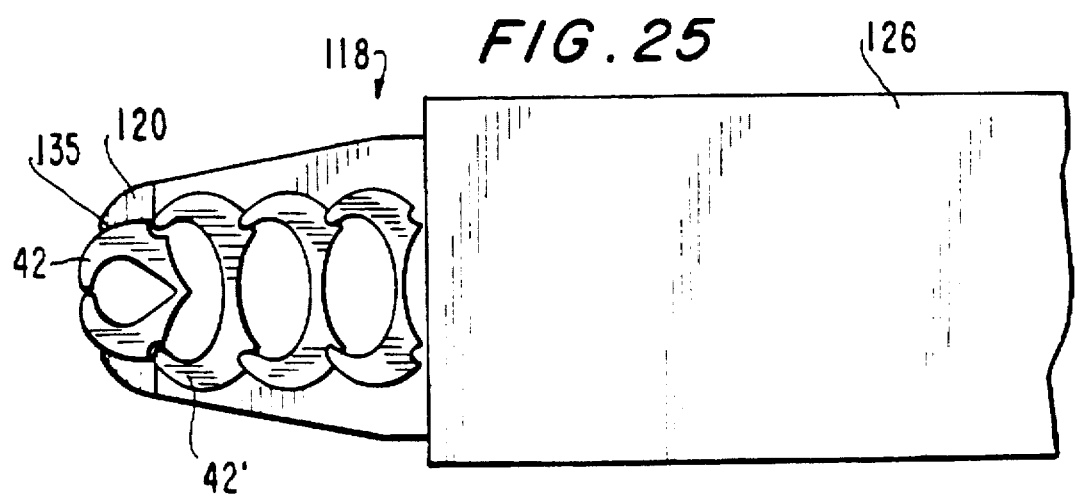
FIG. 25 shows a detailed top view of a clip loaded and formed in the jaws of the instrument of FIG. 17.

Turning now to the jaw blade assembly 114 for forming the clip 42 and with reference to FIGS. 17, 18, and 23 jaw blade assembly 114 includes an elongated jaw blade 116 which has a pair of jaws 118 formed at a bifurcated distal end for receiving a surgical clip therein. Each jaw 118 receives a leg of the substantially C-shaped surgical clip 42 from the series of clips 158. Each jaw 118 also includes raised portions 120 which act in a manner similar to raised portions 39 as described above, as a stop for the clip 42 to enhance formation thereof. The raised portions 120 include an arcuate portion 135 which conforms in shape to the leg of the clip 42, as seen in FIGS. 24 and 25. Arcuate portion 135 arrests forward or distal movement of the distalmost clip 42 as series of clips 158 is urged distally by spring 148. The jaw blade 116 has a pair of camming surfaces 124 which are engaged by channel assembly 126 to close the jaw 118 in a manner described below. The jaws 118 are bent at an angle of approximately 30 degrees to enhance visibility of the structure to which the clip 42 is being applied. Another feature of the jaws 118 is that they are flexible and deformable and preferably formed of stainless steel.

The jaw blade assembly 114 also includes along its elongated portion a clip carrier portion 128 upon which series of clips 158 are positioned. Clips 158 are retained in the side walls 170 of the clip cover 122, shown in FIGS. 19 and 20. In this embodiment the clip carrier portion 128 is integral with the jaw blade assembly 114, although multiple elements could be used to achieve the same result. Jaw assembly 114 also is provided with keyway slot 250 whose purpose will be described below.

Figure 19A:
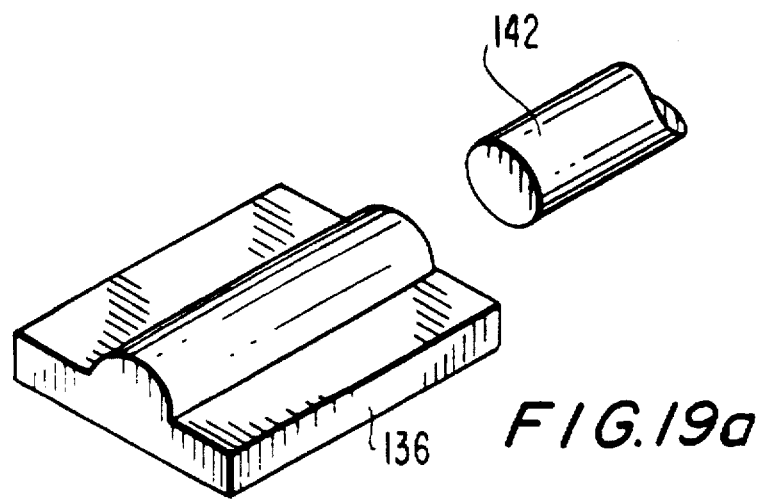
FIG. 19a is a perspective view of the indicator for showing the number of clips remaining in the clip series.
Figure 19B:
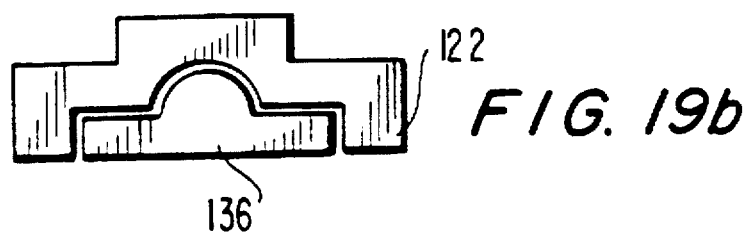
FIG. 19b is a side cross-section of the indicator in position in the clip cover of FIG. 19.
Figure 19:
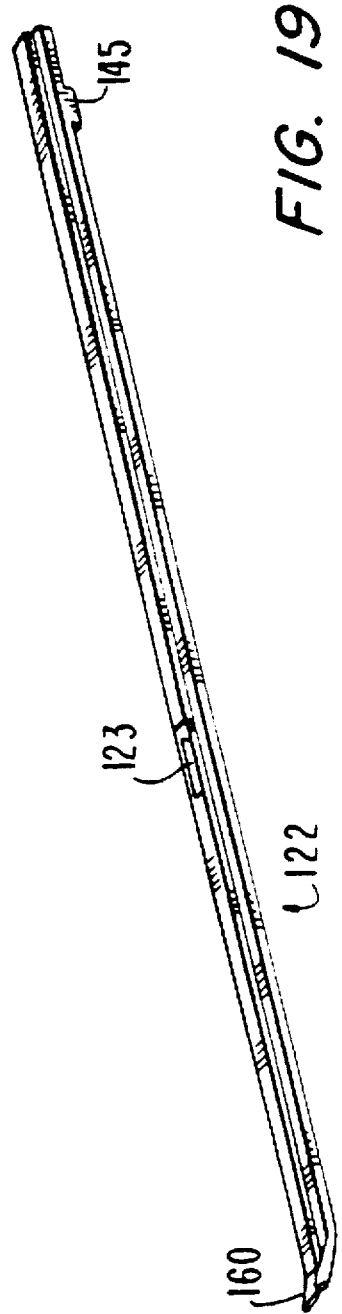
FIG. 19 is an enlarged perspective view of the clip cover assembly of FIG. 17.
Figure 20:
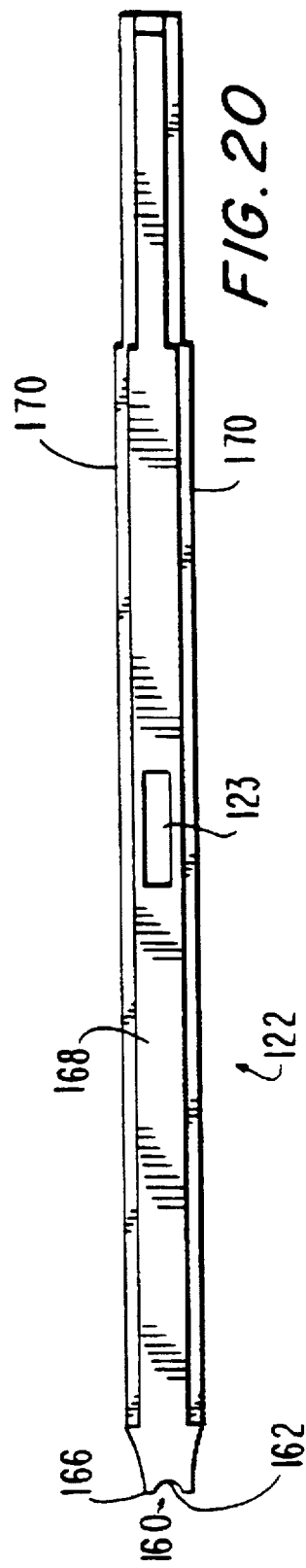
FIG. 20 is an enlarged bottom view of the clip cover assembly of FIG. 19.

Clip cover 122, shown in FIGS. 17, 19 and 20 is elongated and similar in shape to the jaw blade assembly 114 and includes a tissue stop 160. The tissue stop 160 extends distally over the jaws 118, and has a bifurcated distal end which overlies and serves as a guide to prevent tissue from moving the clip 42 proximally and out of raised portions 120. The tissue stop 160 has a rounded cut out 162, and a pair of rounded ends 166 at its distal end. The bottom surface 168 of the clip cover 122 is positioned atop jaw blade assembly 114 and includes a pair of downwardly extending side walls or rails 170 between which the series of clips 158 are retained and the pusher bar 134 and indicator 136 are provided. Indicator 136 is shown in detail in FIG. 19a and its position within clip cover 122 is shown in FIG. 19b. The distal end of the clip cover 122 includes a pair of downwardly extending key portions 145 which engage cut outs 147 in the jaw blade assembly 114.

Referring to FIGS. 16 and 17, the channel assembly 126, which as mentioned above functions to cam jaws 118 closed, is U-shaped and includes a reduced height portion 172 at its proximal end for engagement with the rotation knob 138 at keyway slot 251a as will be described below. Channel 126 also has at its proximal end a transverse slot 164 for engaging a link 144 as will be described below. The channel 126 envelops the jaw blade assembly 114 and includes a pair of upstanding walls 174, 176 and a bottom wall 175. The side walls 174, 176 each include an inturned flange 178, 180, respectively, at its top side, formed therein for engagement around the top surface of clip cover 122. Inturned flanges 178 and 180 serve to lock the assembly together, which includes cover 122, series of clips 158, pusher bar 134, indicator 136, jaw assembly 118 and rod 142. The reduced height portion 172 of the channel assembly 126 includes slot 164, and reduced height portion 172 extends through a passageway 184 in the knob 138 and matingly engages corresponding annular flange 186 formed in the link 144 to permit rotational movement of the entire assembly by knob 138.

Figure 22:
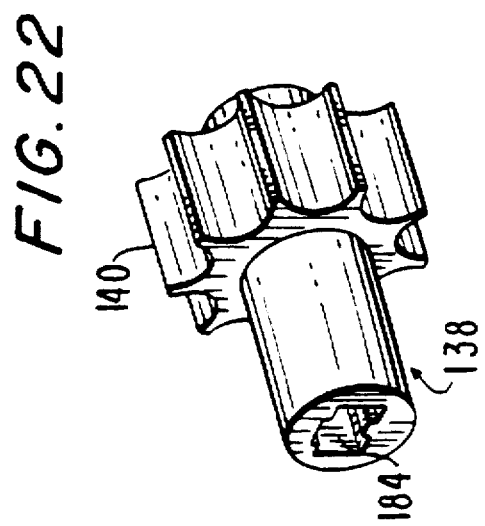
FIG. 22 is an enlarged perspective view of the knob of FIG. 17.
Figure 22A:
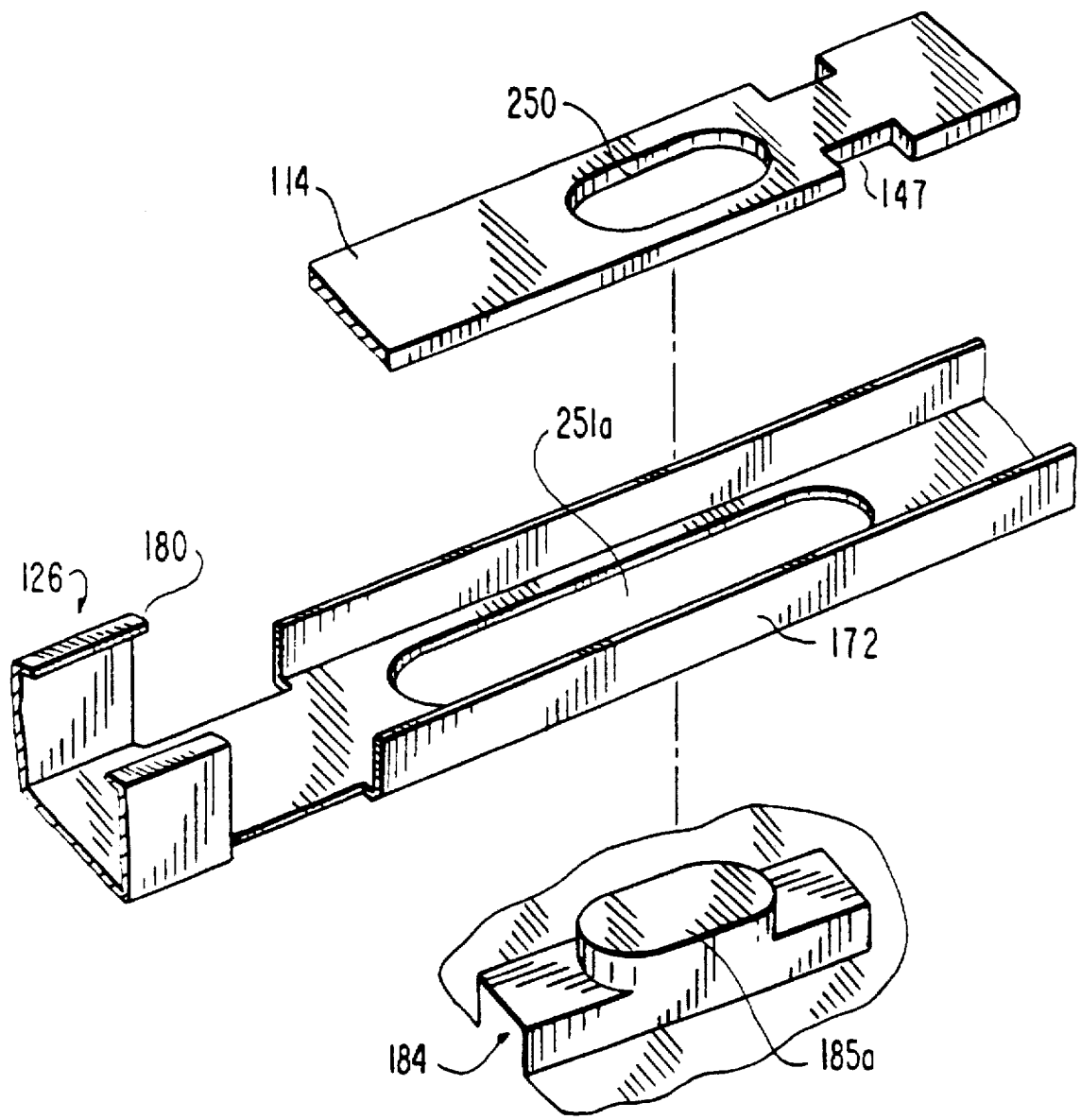
FIG. 22a is an enlarged, exploded perspective of the keyway connection between the knob of FIG. 22 and the channel assembly 126 and jaw assembly 114 of FIG. 17.

Referring to FIG. 22a, there is shown the keyway connection between knob 138 within passageway 184 with channel assembly 126 and jaw assembly 114. Jaw assembly 114 is provided with a keyway slot 250 which matingly engages keyway post 185a in a secure manner. Keyway post 185a passes through slot 251a in channel assembly 126 so that the channel assembly may slide in response to movement of the handles. Keyway slot 250 locks jaw assembly 114 against longitudinal movement, but permits rotational movement due to knob 138. Channel assembly 126 is permitted to slide over post 185a and through knob 138 to crimp a clip in jaws 118 as described below, due to the provision of slot 251a. As can be appreciated, slot 251a is longer and wider than slot 250, and post 185a as well.

Elongated pusher bar 134 has a plurality of transversely extending grooves 135 in its distal end to provide flexibility as it advances up the approximately 30 degree incline of the jaws 118 to feed the last few clips to the jaws. Otherwise the pusher bar 134 is similar to pusher bar 90 as is shown in FIG. 10 for engaging and pushing the last and most proximal clip of series 158 on the clip carrier 128. A coil spring 148 fits within the molded contours of bottom housing 102 and cooperates with the spring guide block 146 to bias and advance rod 142, which in turn advances indicator 136 and pusher bar 134 distally, thereby advancing series of clips 158.

Link 144 is provided and facilitates both rotational movement and longitudinal movement. Link 144 translates longitudinal actuation of the forming cam 154 into movement of the channel 126. An annular flange 186 in the link 144 engages slot 164 in the channel assembly 126 to longitudinally actuate the channel 126 in response to movement of the handles. It should be noted that while the flange 186 and slot 164 engagement permits movement of the channel assembly 126 along its longitudinal axis, the slot 164 is also free to rotate about the annular flange 186 in response to rotation of the knob 138, thus rotating the entire assembly. A rod 142 extends, and moves longitudinally through the link 144, but is not actuated by the link. The proximal end of the rod 142 engages the spring guide block 146 to translate the bias or tension of the spring 148 to the pusher bar 134 by its abutment at its distal end to the clip indicator 136 as shown in FIGS. 19a and 19b, and hence pusher bar 134. Forming cam 154 is secured to link 144 by arms 155, which fit about link 144 and into cutouts 196, as described below.

Figure 21:
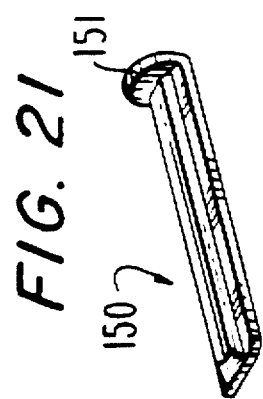
FIG. 21 is an enlarged perspective view of the wedge of FIG. 17.

Referring now to FIGS. 17 and 22, the knob 138 retains the proximal ends of and rotates the entire distal assembly including the jaw blade assembly 114, the series of clips 158, the clip indicator 136, the pusher bar 134, the channel 126 and the clip cover 122. The knob 138 receives a wedge 150 as shown in FIG. 21 which provides a friction fit of the jaw blade assembly 114 and clip cover 122 within the knob 138, thereby enabling their rotation in response to rotation of the knob 138 but permitting longitudinal movement of pusher bar 134 and channel 126.

Turning now to the operation of the device 100, each handle 101, 103 is articulated to the housings 102 and 104 and is operable to effect movement of the channel assembly 126. Handles 101, 103 are pivotally connected to opposite sides of the housings 102, 104 and engage pins 108 which ride along cam slots 156 of forming cam 154. The forming cam 154 is connected by a pair of arms 155 at its distal end to the cutouts 196 of the link 144. As indicated in FIG. 17, the channel assembly 126 is mounted at slot 164 to the distal end of link 144 at flange 186 while the proximal end of link 144 is attached at cutouts 196 to the distal end of forming cam 154 at arms 155. Thus, when handles 101, 103 close together against the biasing of spring 107, the pins 108 move along slots 156 of forming cam 154 to distally advance the forming cam 154 which correspondingly advances link 144 and the channel assembly 126. Channel assembly 126 engages jaws 118 of jaw assembly 114 at camming surfaces 124 to close the jaws.

In use, the clip applier 100 is provided with a clip 42 already in the jaws 118 of the jaw blade assembly 114. To apply the clip 42, the handles 101, 103 are first squeezed together overcoming the bias of spring 107 and causing the channel assembly 126 to move distally as described above and over jaws 118 of the jaw blade assembly 114. As best shown in FIG. 25, this movement over the jaws 118 cams the jaws 118 closed causing the raised portions 120 of the jaws 118 to form the clip 42 therein. The flexibility of the jaws 118 prevents trauma to tissue in which the clip 42 is being applied by not further forming the clip 42 or damaging tissue once the clip 42 has been formed. This trauma is prevented by the jaw arms 149 which absorb the overstroke and deflect once the clip 42 has been fully formed and the jaws 118 are closed, but the channel assembly is still advancing. As the handles 101, 103 open, the formed clip 42 is released from the jaws 118, and the pusher bar 134 is advanced distally to advance the next clip 42' to the jaws 118. The clip is retained in the jaws by the raised portions 120 and arcuate portion 135. The clips are urged forward as a group, and are held from being forced back in a proximal direction by each other in conjunction with pusher bar 134. The clip indicator 136 may be viewed through the window 123 on the clip cover 122 to display approximately how many clips in series 158 are left in the device 100.

Turning to the embodiment shown in FIG. 26, there is illustrated an endoscopic clip applier for the application of microclips in an endoscopic or laparoscopic surgical procedure. Heretofore, although prior art devices have been developed for the application of surgical clips in endoscopic surgical procedures, it has not been possible to store multiple clips and individually apply microclips (without individually loading each clip) during such procedures due to the minute size of the clips and the correspondingly small size of the components of the clip applier. The device of FIG. 26 provides such a microclip applier, particularly suited for endoscopic and laparoscopic microsurgical procedures.

Referring to FIGS. 26 and 27, instrument 400 is provided which includes endoscopic body portion 402 for accessing remote surgical sites in endoscopic or laparoscopic surgical procedures. Instrument 400 is substantially identical to instrument 100 as described above with reference to FIGS. 16-25, except for the elongated portion defined by endoscopic body portion 402 and the elongation of the channel 172 and rod 142 disposed therein. As seen in FIG. 27, endoscopic body portion 402 includes top tube portion 404 and bottom tube portion 406, which substantially enclose the clip applying mechanism which includes channel assembly 126, jaw assembly 114, series of clips 158, pusher bar 134, indicator 136 and clip cover 122. Bottom robe 406 includes keyway post 185b which passes through slot 251b in channel assembly 126, and is matingly engaged in a secure manner in slot 250 to permit longitudinal movement of channel assembly 126 while preventing longitudinal movement of jaw assembly 114. This permits channel assembly 126 to move to crimp a clip positioned in jaws 118. As explained with reference to FIG. 22a above, slot 251b is wider and longer than post 185b and slot 250 in jaw assembly 114. With reference to FIGS. 27 and 22a, slot 250a engages post 185a in knob 138 to secure the endoscopic body portion 402 to knob 138 to facilitate rotation of body portion 402.

A seal device such as O-ring 408 is provided and is positioned within endoscopic body portion 402 substantially enclosing the assembly formed by clip cover 122, series of clips 158, pusher bar 134, jaw assembly 114 and channel assembly 126. O-ring 408 substantially surrounds these components and is wedged between top tube portion 404 and bottom tube portion 406 to prevent the leakage of gas through the instrument during the endoscopic surgical procedure.

Typically, in an endoscopic surgical procedure, the cavity is insufflated with gas such as carbon dioxide to inflate the cavity to permit the surgeon to access the surgical objective without interference from adjacent tissue and organs. Accordingly, it is desirable to provide some sort of seal means in the endoscopic portion of the instrumentation to prevent the inadvertent leakage of the insufflation gas through the instrument itself. O-ring 408 is shown for illustration purposes only, and it is contemplated that any suitable seal mechanism may be provided within endoscopic body portion 402.

FIG. 28 illustrates the present instrument in use during an endoscopic surgical procedure. After the body cavity is insufflated, a trocar assembly is utilized to puncture the body wall 414 to provide access for the surgical instrumentation to perform the endoscopic or laparoscopic surgical procedure. After the trocar assembly is put in place, the instrument is inserted through trocar housing 410 and trocar cannula 412 and exits the trocar assembly adjacent the surgical site. In the illustration shown in FIG. 28, a pair of severed vessels, typically a blood vessel, are to be rejoined. The vessels are placed adjacent each other and their ends everted by the surgeon using instrumentation suited for this purpose. Once the everted ends 420 are placed adjacent each other, the instrument is utilized to apply clips 42 about the circumference of the everted vessels to join them together. The surgeon will apply as many clips as necessary to rejoin the severed vessels 416 and 418.

FIGS. 29 and 30 illustrate the present invention in operation. FIG. 29 illustrates the instrument in the at rest condition where the jaw assembly 114 is positioned adjacent a pair of vessels 416 and 418 to be joined. The everted ends 420 are placed side by side and the jaw assembly positioned over the everted ends to apply the microclip. As seen in FIG. 29, handles 101, 103 are in their at rest condition where pins 108 are at the distalmost position in slots 156 of forming cam 154. The distal end of forming cam 154, namely arms 155, engage the cutouts 196 and link 144, which is further connected as described above to channel assembly 126 at slot 164. Rod 142 passes through link 144 beneath forming cam 154 and engages guide block 146 at its proximal end and indicator 136 at its distal end to urge the series of clip 158 in a distal direction.

In order to crimp a clip 42 positioned in the jaws 118, handles 101, 103 are closed in the direction of arrow "A" as indicated in FIG. 30. As the handles are closed, pins 108 ride in cam slots 156 of forming cam 154 to move forming cam 154 in the distal direction. As this occurs, link 144 is moved in a distal direction which consequently moves channel assembly 126 in the distal direction as indicated by arrow "B". As channel assembly 126 moves in the distal direction, the distal end of channel assembly 126 engages camming surfaces 124 of jaws 118 to cam the jaws closed and crimp the clip 42 positioned therebetween. When handles 101, 103 are released, spring 107 (as shown in FIG. 27) returns the instrument to the position shown in FIG. 29.

Other variations and modifications of the applier may occur to those of skill in the art. It is therefore intended that the foregoing be regarded as merely illustrative, which should be measured by the claims that follow.

What is claimed is:

1. A method for endoscopically performing anastomosis procedures in vascular surgery comprising the steps of:
   (a) inserting a trocar assembly through a body wall to a position adjacent to respective sections of first and second vessel portions;
   (b) everting the respective sections of the first and second vessel portions and positioning the sections in adjacent relation to each other;
   (c) providing a clip applying instrument including a handle assembly, an endoscopic body portion extending distally from the handle assembly, a pair of jaws supported adjacent to a distal end of the endoscopic body portion, and a series of clips;
   (d) inserting the endoscopic body portion through the trocar assembly to a position adjacent to the respective sections of the first and second vessel portions;
   (e) positioning the jaws about a portion of the everted sections of the vessel portions;
   (f) actuating the handle assembly to close the jaws and crimp a clip positioned therebetween;
   (g) releasing the handle assembly to open the jaws and release the crimped clip;
   (h) positioning the jaws of the instrument about an unclipped portion of the everted sections of the first and second vessel portions; and
   (i) repeating steps (f) to (h) to apply a plurality of clips to the everted sections of the first and second vessel portions.

2. A method according to claim 1 wherein the step of positioning the jaws includes rotating the jaws about an axis defined by the longitudinal axis of the endoscopic body portion.

3. A method according to claim 1 wherein the handle assembly includes a pair of handle members, each handle member having a proximal end pivotally mounted to the clip applying instrument, and wherein the step of actuating the handle assembly includes pivoting the handle members towards each other in a tweezer-like manner.

4. A method according to claim 1 wherein step (h) is performed while the endoscopic body portion remains inserted through the trocar assembly.

5. A method according to claim 4 wherein the series of clips is supported within the endoscopic body portion and the step of releasing the handle assembly to open the jaws and release a clip allows the foremost clip of the series of clips to be positioned between the jaws.

6. A method for performing anastomosis procedures in vascular surgery comprising the steps of:
   (a) everting respective sections of first and second vessel portions;
   (b) positioning the everted sections in adjacent relation with respect to each other;
   (c) providing a clip applying instrument including a pair of jaws, a series of clips, each clip having a pair of inwardly directed legs, and a handle assembly operably associated with the jaws to close the jaws upon actuation of the handle assembly;
   (d) positioning the jaws of the instrument over a first portion of the everted sections of the vessel portions;
   (e) actuating the handle assembly to close the jaws and crimp a clip positioned therebetween such that ends of the legs are approximated about the everted sections of the vessel portions to non-invasively join the vessel portions;
   (f) releasing the handle assembly to open the jaws and release the crimped clip;
   (g) positioning the jaws of the instrument over an unclipped portion of the everted sections of the first and second vessel portions; and
   (h) repeating steps (e) to (g) to apply a plurality of clips to the everted sections of the first and second vessel portions.

7. A method according to claim 6 wherein the step of positioning the jaws includes rotating the jaws about a longitudinal axis of the apparatus.

8. A method according to claim 6 wherein the handle assembly includes a pair of handles, each handle being pivotally mounted at a proximal end to the clip applying instrument, and wherein the step of actuating the handle assembly includes pivoting the handles towards each other in a tweezer-like manner.

9. A method for performing anastomosis procedures in vascular surgery comprising the steps of:
   (a) everting respective sections of first and second vessel portions;
   (b) positioning the everted sections in adjacent relation with respect to each other;
   (c) providing a clip applying instrument including a jaw assembly having a pair of jaws, a series of clips, and a handle assembly having a pair of handle members, each handle member being pivotably connected at its proximal end to the instrument;
   (d) positioning the jaws of the instrument about a first portion of the everted sections of the vessel portions;
   (e) pivoting each of the handle members inwardly towards each other in a tweezer-like manner to close the jaws and crimp a clip positioned therebetween;
   (f) releasing the handle members to allow the jaws to open and release the crimped clip;
   (g) positioning the jaws of the instrument about an unclipped portion of the everted sections; and
   (h) repeating steps (e) to (g) to apply a plurality of clips to the everted sections of the first and second vessel portions.

10. A method according to claim 9 wherein the step of positioning the jaws of the instrument includes rotating the jaws about a longitudinal axis of the instrument.

11. A method for endoscopically performing anastomosis procedures in vascular microsurgery comprising the steps of:
   (a) inserting a trocar assembly through a body wall to a position adjacent to respective sections of first and second vessel portions;

(b) everting the respective sections of the first and second vessel portions;

(c) positioning the everted sections in adjacent relation with respect to each other;

(d) providing a clip applying instrument including a pair of jaws, an endoscopic body portion extending distally from the handle assembly, a series of microclips supported in end-to-end relation within the endoscopic body portion, and a handle assembly operably associated with the jaws to close the jaws upon actuation of the handle assembly;

(e) inserting the endoscopic body portion through the trocar assembly;

(f) positioning the jaws of the instrument over a first portion of the everted sections of the vessel portions;

(g) actuating the handle assembly to close the jaws and to crimp a microclip positioned therebetween;

(h) releasing the handle assembly to open the jaws and release the crimped microclip and to allow the foremost microclip of the series of microclips to be positioned between the jaws;

(i) positioning the jaws of the instrument over an unclipped portion of the everted sections of the first and second vessel portions; and (j) repeating steps (g) to (i) to apply a plurality of microclips to the everted sections of the first and second vessel portions.

12. A method according to claim 11 wherein step (h) is performed while the endoscopic body portion remains inserted through the trocar assembly.

13. A method according to claim 11 wherein the step of positioning the jaws of the instrument includes rotating the jaws about an axis defined by the longitudinal axis of the endoscopic body portion.

14. A method according to claim 11, wherein the handle assembly includes a pair of handle members, each handle member having a proximal end pivotally mounted to the clip applying instrument, and wherein the step of actuating the handle assembly includes pivoting the handle members towards each other in a tweezer-like manner.

* * * * *